(12) United States Patent
Schwertner

(10) Patent No.: US 7,977,625 B2
(45) Date of Patent: Jul. 12, 2011

(54) METHOD AND ASSEMBLY FOR OPTICAL REPRODUCTION WITH DEPTH DISCRIMINATION

(76) Inventor: Michael Schwertner, Jena (DE)

( * ) Notice: Subject to any disclaimer, the term of this patent is extended or adjusted under 35 U.S.C. 154(b) by 0 days.

(21) Appl. No.: 12/450,759

(22) PCT Filed: Apr. 11, 2008

(86) PCT No.: PCT/EP2008/054390
§ 371 (c)(1),
(2), (4) Date: Dec. 29, 2009

(87) PCT Pub. No.: WO2008/125605
PCT Pub. Date: Oct. 23, 2008

(65) Prior Publication Data
US 2010/0108873 A1    May 6, 2010

(30) Foreign Application Priority Data

Apr. 13, 2007 (DE) .......................... 10 2007 018 048

(51) Int. Cl.
*G01D 18/00* (2006.01)
(52) U.S. Cl. ..................................... 250/252.1
(58) Field of Classification Search ............... 250/252.1, 250/459.1
See application file for complete search history.

(56) References Cited

U.S. PATENT DOCUMENTS

| | | | |
|---|---|---|---|
| 3,013,467 A | 12/1961 | Minsky | 88/14 |
| 5,381,236 A | 1/1995 | Morgan | 356/376 |
| 5,926,283 A | 7/1999 | Hopkins | 356/419 |
| 6,376,818 B1 | 4/2002 | Wilson et al. | 250/201.3 |
| 6,687,052 B1 | 2/2004 | Wilson et al. | 359/385 |
| 6,819,415 B2 | 11/2004 | Gerstner et al. | 356/124 |
| 7,115,848 B1 | 10/2006 | Zinter et al. | 250/201.3 |
| 7,170,696 B2 | 1/2007 | Wolleschensky | 359/831 |
| 7,193,773 B2 | 3/2007 | Haisch et al. | 359/376 |

FOREIGN PATENT DOCUMENTS

| | | |
|---|---|---|
| DE | 10118463 | 10/2002 |
| EP | 1333306 | 8/2003 |
| EP | 1 420 281 | 5/2004 |
| JP | 2001117010 | 4/2001 |

(Continued)

OTHER PUBLICATIONS

R. Heintzmann, "Structured illumination Methods," 2006, Handbook of Biological Confocal Microscopy, pp. 265-279.*

(Continued)

*Primary Examiner* — David P Porta
*Assistant Examiner* — Kiho Kim
(74) *Attorney, Agent, or Firm* — Gerald T. Bodner

(57) ABSTRACT

A method and an assembly for generating optical section images permit the three-dimensional, layered optical scanning of spatially extended objects. Illumination patterns with periodicity in at least one direction are projected into a plane and the light from the sample which is reflected and/or scattered and/or emitted fluorescence light is being imaged onto a spatially resolving detector. Initially, there is a calibration step, in which the local phase and/or the local period of the illumination patterns are determined for each location on the detector. In the sample detection mode, for the calculation of each optical section image there are two illumination patterns projected into or onto the sample and the resulting intensity distributions are used to form an image on the detector.

13 Claims, 18 Drawing Sheets

FOREIGN PATENT DOCUMENTS

| JP | 2001330555 | 11/2001 |
|---|---|---|
| WO | WO02/12945 | 2/2002 |
| WO | WO03/060587 | 7/2003 |

OTHER PUBLICATIONS

Ansari et al., "High frame-rate, 3D photorefractive holography through turbid media with arbitrary sources, and photorefractive structured illumination," 2001, IEEE Journal on selected topics in qunatum electronics, vol. 7, No. 6, pp. 878-886.*

Krzewina, et al.: "Single-exposure optical sectioning by color structured illumination microscopy", Optics Letters, Optical Society of America, vol. 31, No. 4, Feb. 15 2006, pp. 477-479.

Neil, et al.: "Method of obtaining optical sectioning by using structured light in a conventional microscope", Optics Letters, Optical Society of America, vol. 22, No. 24, pp. 1905-1907, Dec. 15, 1997.

Neil, et al.: "Real time 3D fluorescence microscopy by two-beam interference illumination", Optics Communications, vol. 153, pp. 1-4, Jul. 15, 1998.

Schaefer, et al.: "Structured illumination microscopy: artefact analysis and reduction utilizing a parameter optimization approach", Journal of Microscopy, vol. 216, Part 2, pp. 165-174, Nov. 2, 2004.

Chenggen Quan, et al.: "Shape measurement by use of liquid-crystal display fringe projection with two-step phase shifting", Applied Optics, vol. 42, No. 13, pp. 2329-2335, May 1, 2003.

Webb, et al.: "A wide-field time-domain fluorescence lifetime imaging microscope with optical sectioning", Review of Scientific Instruments, vol. 73, No. 4, pp. 1898-1907, Apr. 2002.

Sieracki, et al.: "Simple binary optical elements for aberration correction in confocal microscopy", Optics Letters, Optical Society of America, vol. 20, No. 10, May 15, 1995, pp. 1213-1215, May 15, 1995.

Korner, et al.: "One-grating projection for absolute three-dimensional profiling" Optical Engineering, Society of Photo-Optical Instrumentation Engineers, Opt. Eng. 40(8), Aug. 2001, pp. 1653-1660.

Notification of Transmittal of the International Preliminary Report on Patentability, the International Preliminary Report on Patentability and the Written Opinion of the International Searching Authority dated Nov. 19, 2009.

* cited by examiner

US 7,977,625 B2

METHOD AND ASSEMBLY FOR OPTICAL REPRODUCTION WITH DEPTH DISCRIMINATION

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION (1) Field of the Invention

The invention relates to a method and an assembly for generating optical section images.

(2) Description of Related Art

In order to create three-dimensional images or mappings of objects, one often uses the technique of optical sectioning. A so-called optical section is an image, which contains information from a certain range of depth. Therefore, an optical system for the generation of optical section images performs selective imaging of those object details which are within the focal plane, while object details outside the focal plane are suppressed in the optical section image.

By means of recording of a series of optical section images located at different focal positions one can scan a three-dimensional object step by step. Thus a three-dimensional representation of an object or its topography can be analysed. In the following, the terms object and sample are used interchangeably. Especially in microscopy, the object investigated is often referred to as the sample.

One of the first methods for the generation of optical section images was the confocal microscope described in U.S. Pat. No. 3,013,467 entitled "Microscopy Apparatus", which issued to Marvin Minsky in 1961 (hereinafter referred to as Reference No. 1). Here the imaging of details from outside the focal plane is suppressed by an arrangement of confocal pinholes.

Another approach for the generation of optical section images is structured illumination, as for example described in the article "Method of Obtaining Optical Sectioning by using Structured Light in a Conventional Microscope" by M. A. A. Neil, R. Juškaitis and T. Wilson, Optics Letters, Vol. 22, No. 24, p. 1905, 1997 (hereinafter referred to as Reference No. 2). Here, a structure, for example a grating, is projected into the sample to be imaged. This, in turn, creates a modulation of the light distribution within the sample. As is for example shown in Reference No. 2, the modulation depth has its largest value in the focal plane and marks the focal plane in that sense. In structured illumination the first step is to impose a modulation onto the illumination light, followed by a recording of different positions (phase steps) of the projected structure, where finally the optical section image is calculated from the recorded data.

For this purpose several arrangements were proposed. In U.S. Pat. No. 6,376,818, entitled "Microscopy Imaging Apparatus and Method", which issued to Wilson, et al. in 2002 (hereinafter referred to as Reference No. 3), a grating is placed in a plane conjugated with the sample and moved perpendicular to the optical axis. In the different design described in U.S. Pat. No. 6,819,415, entitled "Assembly For Increasing the Depth Discrimination of an Optical Imaging System", which issued to Gerstner, et al. in 2004, and in PCT Patent Publication No. WO02/12945, entitled "Assembly for Increasing the Depth Discrimination of an Optical Imaging System", published in 2002 and naming Gerstner, et al. as inventors (hereinafter referred to as Reference No. 5), a parallel plate is inserted into the beam path and tilted, which laterally moves the illumination structure projected into the sample. For transparent or semi-transparent specimens a projection into the sample takes place while for non-transparent surface structures one refers to a projection onto the sample.

Another solution was proposed in the article "Real Time 3D Fluorescence Microscopy by Two-Beam Interference Illumination" by M. A. A. Neil, et al., Optics Communications, 153, 1998 (hereinafter referred to as Reference No. 6). Here, the illumination structure is created directly within the sample by means of interference.

The methods described in References Nos. 2-6 have the property that they require the recording of at least three individual images. All these methods have in common that artifacts and inaccuracies may arise during the positioning and projection of the structure since it requires fast and also accurate setting of a mechanical element. Details on artefacts and their compensation can for example be found in the article "Structured Illumination Microscopy: Artefact Analysis and Reduction Utilizing a Parameter Optimization approach" by Schaefer, Journal of Microscopy 216 (2), 165-174, 2004 (hereinafter referred to as Reference No. 7).

The different proposals for the implementation of the method differ with respect to the arrangement used to perform the change of the position of the illumination structure (phase setting). In particular, there are arrangements proposed without moving parts which, therefore, allow fixed alignment and a very good reproduction of the phase steps.

In U.S. Pat. No. 5,381,236, entitled "Optical Sensor for Imaging an Object", which issued to Cohn G. Morgan (hereinafter referred to as Reference No. 11), an optical sensor for range finding of three-dimensional objects is described. Here, a periodic structure is projected onto the object where the illumination structure can be inverted, which corresponds to a phase shift of 180 degrees. The method proposed here is also based on a change of the illumination structure in two steps, but compared to Reference No. 11 it has the following differences:

In Reference No. 11, the individual elements of the illumination structure need to be exactly aligned with the individual elements of the detector (CCD pixels). This is a strong restriction for several reasons: the optical arrangement would need to be very accurate in terms of the magnification, to achieve matching of the illumination pattern with the detector. Furthermore, the alignment of the two structures in relation to each other would need to be very accurate and with sub-pixel precision. The probably most important limitation is due to the fact that even a small distortion in the optical image (e.g. a barrel or a pincushion distortion) makes it impossible to match the elements of the illumination pattern with those of the detector at a sub-pixel level for the whole field of view.

The arrangement would require highly corrected and well adjusted optics, which would be an obstacle to widespread and robust applications.

For the proposed method, as opposed to Reference No. 11, the illumination pattern may be chosen freely with respect to type and pattern size because no exact matching of illumination pattern and detector is required. This allows adjusting the depth discrimination of the optical system, e.g. the thickness of the optical section generated (in a confocal microscope system this would correspond to the adjustment of the diameter of the confocal pinhole). With the present invention, this can be easily accomplished while it is impossible with the design in Reference No. 11 according to the state of the art. Therefore, characteristic disadvantages of Reference No. 11 can be avoided. An arrangement without moving parts can avoid disadvantages caused by position-inaccuracies and is also not disclosed in Reference No. 11.

At this stage, for a clear definition and separation from other, conceptually different methods for the measurement of surfaces based on structured illumination described in the literature are referenced. There are surface measurement methods based on triangulation in combination with structured illumination. As an example in the article "Shape Measurement by Use of Liquid-Crystal Display Fringe Projection with Two-Step Phase Shifting" by Chenggen Quan, et al., Applied Optics, Vol. 42, No. 13, 2003, 2329-2335 (hereinafter referred to as Reference No. 12) and further references cited in this document are mentioned. Triangulation evaluates the deformation of an illumination pattern (for example a fringe pattern) during projection onto an object, where the profile of the object is determined from the local phase of the projected pattern. The primary quantity measured is therefore the local phase. It is also characteristic, that projection of the pattern and detection are implemented using separate, non-coaxial optical systems or the object is tilted with respect to the optical axis.

For the present method for optical reproduction with depth discrimination, the goal is the separation (discrimination) of image signals, which originate from the focal plane, from those that correspond to the background. A depth profile of the sample can be obtained by means of axial scanning of the sample using a focussing device, where each of the partial images of the axial scan represents an optical section image. An optical section, sometimes also referred to as pseudo-confocal image, contains image signals from the focal plane only, while background signals are suppressed or removed using appropriate methods. A confocal microscope as described in Reference No. 1 does also produce optical sections; however, the task is accomplished by means of a different optical arrangement. For a method of structured illumination the depth discrimination is based on the detection of the local modulation as the primary quantity measured.

Furthermore, in the present invention, projection of the illumination pattern as well as the detection of the light from the sample is preferably performed through a single optic (objective), which is facing the sample. In contrast to that, triangulation works with projection and detection from different directions.

Another important aspect of implementations of the method of structured illumination with depth discrimination is the use of different wavelengths. Implementations currently known have problems when the wavelength is changed: due to remaining axial chromatic aberration, which may depend on the objective lens and the intermediate optics used, the structure projected (typically a mask) needs to be repositioned in axial direction. This requires relatively large movements within known microscope arrangements and therefore a lot of time for the movement of mechanical elements (see for example Reference No. 4).

The present invention proposes a novel arrangement, which does not require a mechanical axial movement of the projected mask structure anymore and therefore has advantages in terms of speed due to faster time-sequential or even time-simultaneous imaging with different wavelengths. In addition there are new arrangements proposed for the solution of the problem of chromatic correction, which use mechanical components but have lower complexity compared to the state of the art.

Another version of the principle of structured illumination according to the state of the art uses continuously moving illumination masks, which are projected into or onto the sample, are described in U.S. Pat. No. 6,687,052, entitled "Confocal Microscopy Apparatus and Method", which issued to Wilson, et al. in 2004 (hereinafter referred to as Reference No. 8), and European Patent Publication No. EP1420281, entitled "Method and Apparatus for Optical Scanning With a Large Depth of Field", which issued to Ralf Wolleschensky in 2004 (hereinafter referred to as Reference No. 9). Here a moving mask is used for encoding of the illumination structure as well as decoding. For that process it is characteristic, that the light originating from the sample passes the mask. In Reference No. 8, there was an arrangement described which is appropriate for use in a wide-field microscope. The arrangement in Reference No. 9 is predominantly useful in combination with a line scanner. Both methods described in Reference Nos. 8 and 9 have in common that two different signals are integrated on a spatially resolving detector, where the desired optical section image results from a simple subtraction of both image datasets. The arrangements in Reference Nos. 8 and 9 have the disadvantage in common that the light to be detected originating from the sample is attenuated by the mask before it is registered by the detector. This is relevant in particular when weak light signals are observed, which occurs especially in fluorescence microscopy.

In the article "A Wide-Field-Time-Domain Fluorescence Lifetime Imaging Microscope with Optical Sectioning" by S. E. D. Webb, et al., Review of Scientific Instruments, Vol. 73, No. 4, 2002, 1898-1907 (hereinafter referred to as Reference No. 13), it was shown how the method of structured illumination can be combined with the method of fluorescence lifetime measurement. Here the method from Reference No. 2 and Reference No. 3 according to the state of the art is used, which requires the recording of a sequence of three illumination steps. Measurement of fluorescence lifetime is implemented using a combination of a detector with very high temporal resolution (gated optical intensifier) and pulsed laser excitation. A different version for the determination of fluorescence lifetime is "frequency domain FLIM", where the excitation light is modulated periodically and the lifetime is determined from the phase shift of the detected signal with respect to excitation signal. The present invention does also allow measuring the fluorescence lifetime in optical section images with the recording of only two single images per optical section calculated, if appropriate detectors and light sources are used.

The article "Single-Exposure Optical Sectioning by Color Structured Illumination Microscopy" by L. G. Krzewina and M. K. Kim Optics Letters, Vol. 31, No. 4, 2006, 477-479 (hereinafter referred to as Reference No. 14) covers a method for the generation of optical section images from only one image. Here the method using the illumination patterns is implemented as presented in Reference Nos. 2 and 3. During the process, the three illumination patterns projected into or onto the sample and the phase steps from the sample are encoded using light of different wavelengths. This allows time-simultaneous projection and detection. This technique offers advantages in terms of speed, but also creates other problems. The use of fluorescence microscopy is not feasible here since the dyes have pre-determined spectral properties (excitation wavelength and emission wavelength). Furthermore, problems occur when the sample exhibits inhomogeneous spectral properties in reflection mode. Reference No. 14 is therefore considered a special case of the method in Reference No. 2 and Reference No. 3, where limitations occur due to the wavelength encoding of the illumination steps. For the present invention, such limitations are not present since one does not need spectral encoding of the illumination steps.

OBJECTS AND SUMMARY OF THE INVENTION

The present invention relates to a method and an arrangement for the generation of optical section images based on structured illumination and serves the optical scanning of spatially extended objects, layer by layer. Compared to the state of the art it is possible to obtain optical section images by means of projection and recording of two illumination patterns each onto the sample. Furthermore, one should remove the requirement of pixel-wise alignment of the illuminated structure with the detector, which was necessary so far, but hard to fulfil.

The present invention serves the three-dimensional, layer by layer scanning of spatially extended objects with major applications in microscopy, although it is not limited to this field.

The present invention allows the generation of optical section images in a particularly simple way and can be used for analysis of objects, for example, in biology, medicine or in material sciences.

Thus, the invention relates to a method and an assembly for generating optical section images. The invention permits the three-dimensional, layered optical scanning of spatially extended objects and is used in microscopy, but is not limited to this field. In said method, illumination patterns with periodicity in at least one direction are projected into a Plane and the light from the sample which is reflected and/or scattered and/or emitted fluorescence light is being imaged onto a spatially resolving detector.

According to the invention, initially there is a calibration step, in which the local phase and/or the local period of the illumination patterns are determined for each location on the detector. In the sample detection mode, for the calculation of each optical section image there are two illumination patterns projected into or onto the sample and the resulting intensity distributions are used to form an image on the detector. The steps of the procedure to project and detect the two illumination steps can be repeated as required, especially at different focal settings of the sample and/or different exposure wavelengths, where at least one optical section image is calculated from the recorded intensity distributions with the aid of the local phase and/or local period.

The goal of the arrangement is to provide a faster scan of the sample, a more robust construction as well as an improved signal to noise ratio of the optical section images at the same number of detected photons.

In addition an arrangement is proposed, which implements the method according to the invention without moving mechanical parts. This considerably reduces the cost of alignment, cost for mechanical actuators as well as image artefacts due to positioning inaccuracies.

Another aspect of the invention concerns the generation of optical section images, where the sample is scanned using a variety of wavelengths. This may lead to problems with the axial chromatic properties of the optics, which so far has been solved for example by using a mechanical re-positioning of optical elements. There are furthermore arrangements disclosed, which solve the problem of the axial chromatic correction for the structured illumination without the use of mechanical components, especially while integrated within common microscope systems. This leads to further advantages in speed, compared to the state of the art.

In addition, there is a new arrangement for the implementation of structured illumination given, which uses only one actuator for the two tasks of phase shifting of the illumination pattern as well as re-adjustment of the axial chromatic correction.

The method for the generation of optical section images by means of the projection of two illumination patterns is described as follows:

For the structured illumination, the illumination light projected onto the specimen requires to have a modulation in at least one spatial direction. Methods for structured illumination according to the state of the art require at least three illumination patterns or the projection of at least three phase positions of the periodic structures, respectively.

According to the invention, exactly two structures are projected, where it is advantageous if the intensity distribution of the second structure is complementary to the first one and the averaged intensities of both illumination patterns do not differ too much from each other.

Even though the use of two-dimensional illumination patterns is also possible, for the sake of simplicity the principle will be explained using a grating structure. Without limitations to the general case, the projection of a sinusoidal grating structure into/onto the sample is assumed.

The first structure projected into/onto the sample has the form:

$$G_1(a,b) = 1 + A\cos(\omega a + \delta). \qquad <1>$$

The second pattern, which is complementary to the first one, then reads:

$$G_2(a,b) = 1 A\cos(\omega a + \delta) = 1 + A\cos(\omega a + \pi + \delta). \qquad <2>$$

Here a and b are the local lateral coordinates in the system of the pattern projected, $\omega$ is grating frequency and $\delta$ the phase of the grating. As can be seen from <2>, the complementing illumination pattern corresponds to a shift of the periodic pattern by a phase value of $\pi$.

It has to be noted that, according to the present invention, the projection of a pattern and its complementing pattern can be implemented without the use of moving mechanical parts. This eliminates potential phase errors due to inaccuracies in setting the position of mechanical elements and will be discussed later. Furthermore, it is advantageous if the intensities of both projections at the sample averaged across the field of view do not differ too much from each other.

The light patterns $G_1(a,b)$ and $G_2(a,b)$ projected into/onto the sample are scattered, reflected, transmitted, absorbed by the sample or excite fluorescence or luminescence. Arbitrary combinations of the mentioned interactions are also possible, also at a variety of different wavelengths. By means of appropriate configuration of the detectors the fluorescence lifetime can be determined in addition. For this purpose, apart from the high temporal resolution of the detector, pulsed excitation or modulation of the excitation light is required.

The projection of the intensity pattern $G_1(a,b)$ created in the sample is imaged from the location of the sample onto a spatially resolving detector. The intensity distributions $G_1(a,b)$ and $G_2(a,b)$ as well as the object plane (sample) and the detector are located in mutually conjugated image planes. When implemented within a microscope it is advantageous, if the illumination pattern being projected is located in a plane conjugated to the field stop diaphragm.

If $G_1(a,b)$ is projected, the intensity distribution $$I_1(x,y)=K(x,y)+S(x,y)*\cos[x*g(x,y)+\alpha(x,y)] \quad \langle 3 \rangle$$

is measured at the detector. Projection of the second complementing structure $G_2(a,b)$ results in a complementing intensity distribution $$I_2(x,y)=K(x,y)-S(x,y)*\cos[x*g(x,y)+\alpha(x,y)] \quad \langle 4 \rangle$$

at the detector. Here (x,y) are the coordinates in the plane of the detector, $g(x,y)$ is the modulation frequency (grating frequency) in the direction of the x-coordinate, where $g=2\pi/T$ and T is the periodicity in the x-direction. Common spatially resolving detectors, such as CCD's or CMOS sensors are pixel-based. Therefore the coordinates (x,y) can also be specified in discrete pixel coordinates.

The parameter $\alpha(x,y)$ is the phase of the periodic structure. The quantity $K(x,y)$ is the conventional image, which does also contain image information from layers outside the focal plane. In microscopy, $K(x,y)$ corresponds to the wide-field image of the sample.

With the help of equations <3> and <4> the conventional image may be calculated conveniently:

$$K(x,y) = \frac{I_1(x,y) + I_2(x,y)}{2}. \quad \langle 5 \rangle$$

The quantity $S(x,y)$ is the optical section image to be determined, it does also correspond to the modulation depth caused by the structured illumination. The set of equations, consisting of <3> and <4>, contains in total 4 unknown quantities for each location of the detector with the coordinates (x,y): the conventional image $K(x,y)$, the optical section image $S(x,y)$ to be determined, the grating frequency $g(x,y)$ as well as the local phase $\alpha(x,y)$.

In case of perfect geometry of the illumination pattern projected into or onto the sample and in case of perfect imaging conditions, the grating frequency and the phase would not depend on the coordinates (x,y). Under practical conditions and in the presence of slightly imperfect imaging of the optics, this assumption is an approximation only. Therefore, the determination of these local parameters is advantageous or necessary.

The methods according to the state of the art described in Reference Nos. 2-7 assume a locally constant grating frequency. Therefore, three 3 unknown quantities remain and the methods up to now, described in Reference Nos. 2-7, did require the measurement of at least three phase steps a of the projected structure in order to calculate an optical section image.

In the method according to the invention a calibration step is performed, in which the local phase $\alpha(x,y)$ and optionally the local grating frequency $g(x,y)$ is determined from the calibration data measured or the image data $I_1(x,y)$ and/or $I_2(x,z)$ for every location (x,y) in the coordinate system of the detector. In both cases the same methods to be discussed (e.g. Fourier transformation or wavelet-methods) can be used to determine the local phase and the local grating frequency in a certain area. According to the invention, by means of the calibration step or knowledge of the local phase $\alpha(x,y)$ and the local grating frequency $g(x,y)$, respectively, and use of the algorithms described further down, the number of projection steps required for the generation of an optical section image can be reduced to only two. The third or further steps in the sample scanning mode, as are common with other methods according to the state of the art, are obsolete. This leads to reduced sample damage and photo-bleaching, especially in the case of fluorescence microscopy. A calibration measurement preferably uses a flat and homogenous calibration object which reflects and/or scatters and/or has fluorescent and/or luminescent properties. The insertion of the calibration object and the calibration procedure can be automated. The calibration object can be inserted instead of the sample or in an image plane conjugated to the location of the sample.

With the help of the calibration object, a calibration dataset consisting of $C_1(x,y)$ and optional $C_2(x,y)$ during projection of the patterns $G_1(a,b)$ and $G_2(a,b)$, respectively, is recorded for the calibration measurement. With approximately homogenous properties of the calibration object, $C_1(x,y)$ and $C_2(x,y)$, respectively, represent the illumination pattern and its location in the coordinate system of the detector.

If the image datasets $I_1(x,y)$ and $I_2(x,z)$, respectively, are used for the determination of the local phases, these datasets contain sample information onto which the illumination pattern was imposed. Because, the sample properties can vary across the field of view and also between different focal planes under investigation, the quality of the determination of the local phases and the grating frequency can also vary and may be feasible only in certain areas, depending on the sample. If a series of several focal planes is scanned, as it is a common setting, information from several focal planes can be used for the calibration step. For example, the focal plane which allows the determination with the highest quality of the local phases and local grating frequencies, respectively, can be chosen for each detector area. An example criterion for the quality of the determination of the local parameters will be given further down (see metric in <5c>).

Knowledge of the local parameters can, in case of difficulties during the determination in some areas, be extended to the whole coordinate system of the detector by means of interpolation (lateral and/or axial) or by periodic extension. For this process, data from areas with high quality of the determination of the local parameters should be used preferably.

The determination of the local phase $\alpha(x,y)$ and the local grating frequency $g(x,y)$ for a certain area will now be illustrated with an example from a Fourier method. The use of wavelet techniques or iterative procedures is also possible.

The local grating frequency $g(x,y)$ is a continuous function for common arrangements and has slow variations across the field of view only. As an approximation, it can also be determined by the distance E within an image, which is covered by a known number n of periods; then we have $g=n2\pi/E$.

For the more accurate determination we define the quantities $$FT_C(g,x,y) = \int_F \int L(x,y)\cos(g*x)dx\,dy \quad \langle 5b \rangle$$

and $$FT_S(g,x,y) = \int_F \int L(x,y)\sin(g*x)dx\,dy.$$

Here $L(x,y)$ denotes the dataset to be investigated, which can be a dataset from the calibration measurement ($C_1(x,y)$ respective $C_2(x,y)$) or an image dataset ($I_1(x,y)$ respective $I_2(x,z)$). The area of integration F has the coordinates (x,y) as the center and covers, in good approximation, an integer number of periods of the pattern. In case of discrete coordinates (x,y) the integration can be replaced by a summation, accordingly. Now we define the metric $$M(g,x,y) = \sqrt{FT_C^2(g,x,y) + FT_S^2(g,x,y)} \quad \langle 5c \rangle$$

The value of g(x,y) now is exactly the value for which the metric M(g,x,y) delivers a maximum. The value of M(g,x,y) corresponds to the local modulation depth caused by the grating, in case g is the grating frequency. Therefore M(g,x,y) is an additional useful criterion for the quality or accuracy of the determination of the local parameters. The local phase α(x,y) may also be determined, because:

$$\tan[\alpha(x, y)] = \frac{FT_S[g(x, y), x, y]}{FT_C[g(x, y), x, y]}. \quad \langle 5d \rangle$$

The value α(x,y) can now be obtained by inversion of the tangent function where the sign of $FT_S$ respectively $FT_C$ is considered to obtain the quadrant. The function atan2(., .) provided by the programming language C does this automatically.

The determination of the local phases from the image data $I_1(x,y)$ and $I_2(x,z)$, respectively, may lead to slightly less accurate results of the local phases compared to a calibration measurement; however, it allows to omit the calibration measurement and corresponding elements of the arrangement.

The balance between accuracy and spatial resolution of the local parameters can be matched to conditions of the object by choosing the size of the area F accordingly.

In the following it is assumed that the local phase α(x,y) as well as the local grating frequency g(x,y) are known from a calibration step as described or from a-priori knowledge.

For the calculation of the optical section image, using <3> and <4>, the following quantities are introduced:

$$D_1(x, y) = \frac{\partial I_1(x, y)}{\partial x} \quad \langle 6 \rangle$$
$$= -g(x, y) * S(x, y) * \sin[x * g(x, y) + \alpha(x, y)]$$

$$D_2(x, y) = \frac{\partial I_2(x, y)}{\partial x} \quad \langle 7 \rangle$$
$$= +g(x, y) * S(x, y) * \sin[x * g(x, y) + \alpha(x, y)].$$

Now the optical section image to be determined can be conveniently calculated by means of equations <3>, <4>, <6> and <7>:

$$S(x, y) = S(x, y) \sqrt{\cos^2[x * g(x, y) + \alpha(x, y)] + \sin^2[x * g(x, y) + \alpha(x, y)]} \quad \langle 8 \rangle$$

$$S(x, y) = \sqrt{\left[\frac{I_1(x, y) - I_2(x, y)}{2}\right]^2 + \left[\frac{D_1(x, y) - D_2(x, y)}{2 * g(x, y)}\right]^2}.$$

Furthermore, the illumination distribution of both the patterns can be inhomogeneous at the detector. This can be caused by imperfections of the projected structure itself or inhomogeneous properties of the projection into or onto the sample and subsequent imaging onto the detector. According to the invention, the data $I_1(x,y)$ and $I_2(x,y)$ can be normalised to compensate for inhomogeneous properties:

$$N_1(x, y) = \frac{I_1(x, y)}{\overline{C}_1(x, y)}; \quad \langle 9 \rangle$$

$$N_2(x, y) = \frac{I_2(x, y)}{\overline{C}_2(x, y)}.$$

Where $$\overline{C}_1(x, y) = \frac{\int_F \int I_1(x, y) dx dy}{F}; \quad \langle 10 \rangle$$

$$\overline{C}_2(x, y) = \frac{\int_F \int I_2(x, y) dx dy}{F}$$

are the average values of $C_1(x,y)$ ans $C_2(x,y)$, respectively, across an area F, which contains the coordinates (x,y) and covers an integer number of periods of the pattern. The compensation of disadvantageous effects due to inhomogeneous intensities of the illumination patterns (illumination problem or mask imperfections) or inhomogeneous properties of the detector can be compensated by the use of the normalised quantities $N_1(x,y)$ and $N_2(x,y)$ instead of the recorded quantities $I_1(x,y)$ and $I_2(x,y)$ in the equations <5, 6, 7, 8>.

The calculation of optical section images by means of projection and detection of two illumination distributions for each optical section image during the sample scanning mode was demonstrated here using a simplified example of the projection of a continuously variable, sinusoidal illumination pattern. Often, binary patterns are also used because such masks can be manufactured at lower cost. For the reduction of imaging artefacts related to the use of binary or other masks the knowledge of the local phases of the illumination structure is also important and can be accomplished by the calibration step.

The method described can be realised in a variety of arrangements, especially in wide-field fluorescence microscopes and wide-field microscopes for the investigation and depth profiling von surfaces in EPI-configuration (reflection mode).

In the following, drawings and arrangements for the implementation of the method according to the invention will be discussed.

DETAILED DESCRIPTION OF THE PREFERRED EMBODIMENTS

Figure 1:
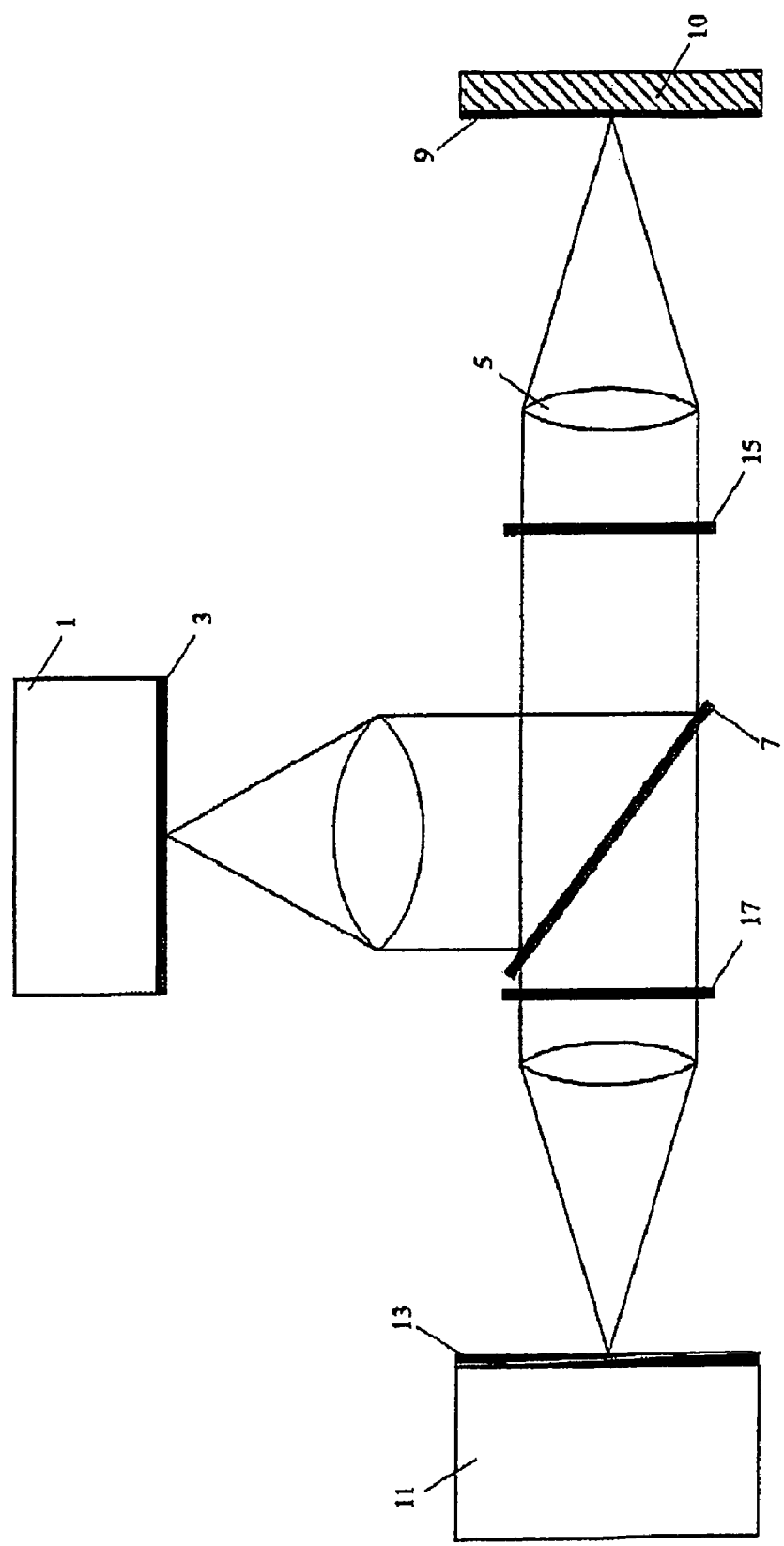
FIG. 1 is a block diagram which shows a simplified arrangement for the implementation of the method of the present invention.

FIG. 1 shows a simplified arrangement for the implementation of the method. For the sake of simplicity, optional intermediate images and relay optics were not drawn. According to the invention, the illumination unit (1) generates two different illumination patterns. Therefore, an illuminated mask structure, an illuminated DMD chip (digital mirror device, also known as DLP technology by Texas Instruments) or an intermediate image of a light distribution is located in plane (3) and has a modulation in at least one spatial direction.

Because the term mask or mask structure is used very often within this document, it should be specified more closely: a mask is an optical element, where the physical properties, especially transmission and/or reflection and/or absorption and/or the optical path difference are patterned across the area of the element. If the optical path difference was patterned, one talks about a phase mask which, for example, can be fabricated by etching of structures into a glass substrate. An illuminated phase mask can create a certain light distribution due to diffraction and may achieve high optical efficiency. All types of mask mentioned here are in the following referred to as the common term mask.

The light distribution present in plane (3) is projected onto or into the object (10) (sample) via the beam splitter (7) and the objective (5). Here the planes (3) and the nominal object plane (9) are conjugated with respect to each other. The beam splitter (7) can be a semi-transparent mirror or a dichroic beam splitter. Multi-band beam splitters can also be used. The light distribution projected into or onto the sample is now imaged onto a detection unit (11), using an objective and further intermediate optics. Plane (13) is an image plane or intermediate image plane, which is conjugated with planes (9) as well as (3). The location of the focal plane within the object may be set using a focussing unit, which is typically realising an axial movement of the objective (5) or the sample. In a microscope system it is advantageous if plane (3) containing the light distribution to be projected, is conjugated with the plane of the field stop diaphragm. Within the detection unit (11) may contain a spatially resolving detector, such as a CCD or a CMOS sensor. As an alternative to that, unit (11) may also image the light in plane (13) further onto one or more detectors.

Figure 2:
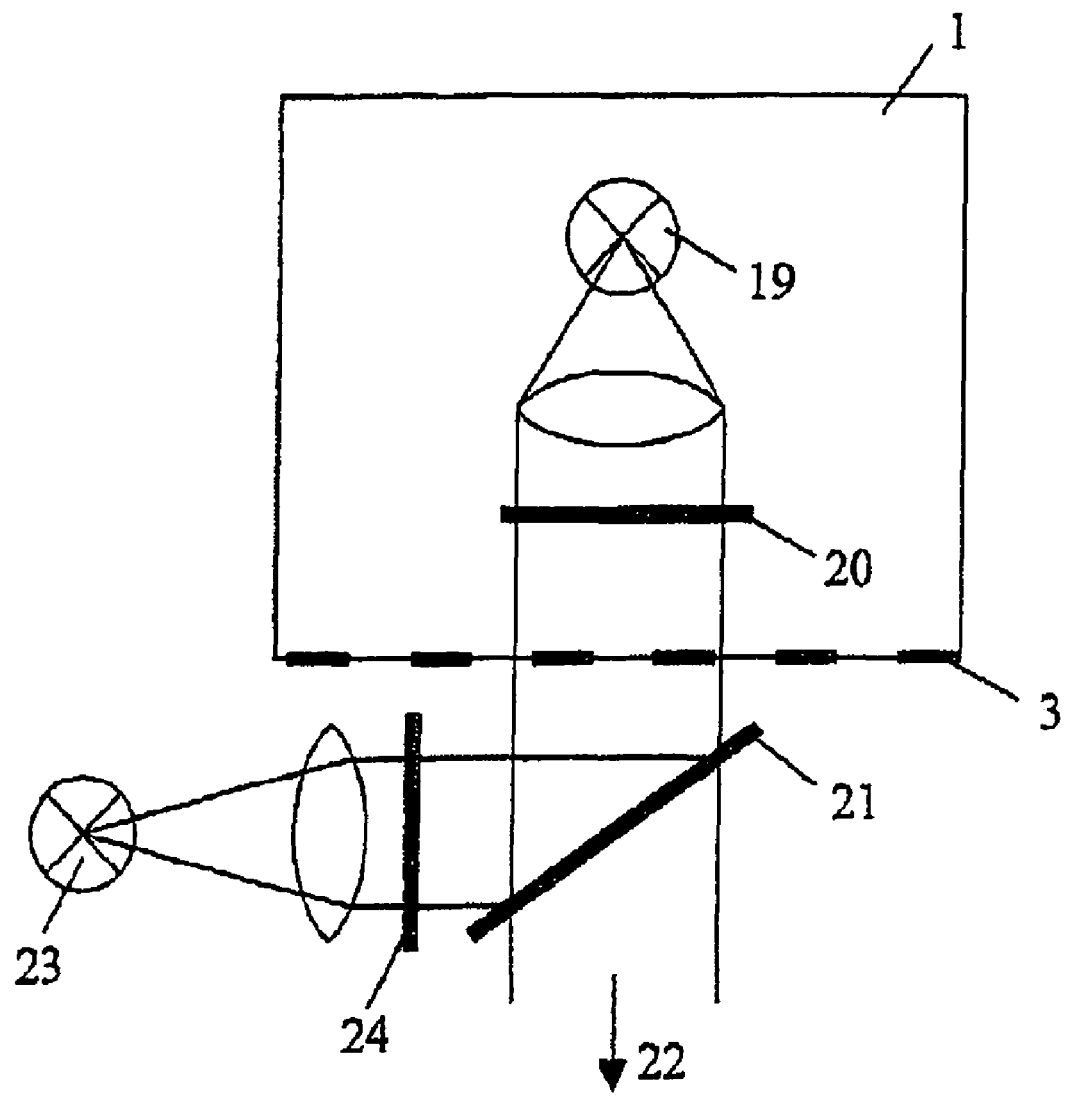
FIG. 2 is a block diagram which shows an arrangement of the illumination unit formed in accordance with the present invention.

FIG. 2 shows an arrangement of the illumination unit (1) according to the invention. The light sources (19) and (23) are arranged such that a mask structure in plane (3) can be illuminated from different sides, using the beam splitter (21). The intensity and optionally the spectral composition of the light emitted by the light sources (19) and (23) can be controlled. In case the mask structure in plane (3) is illuminated from both sides at the same time, the light sources (19) and (23) can also be replaced by a single light source, which by means of a beam splitter and appropriate beam paths illuminates the mask from both sides.

The mask in plane (3) has areas with very high reflectivity and other complementing areas with very high transmission. Such a mask may not only contain binary structures but also continuous distributions. In plane (3) a patterned mirror surface may be located. Thus the two light sources create two illumination distributions complementing each other by means of transmission (light source (19)) and reflection (light source (23)) at the mask structure in plane (3).

It should be pointed out that such an arrangement provides two different illumination patterns allowing the simultaneous or time-sequential projection of two structures or two phase settings of the same structure, respectively, without any moving mechanical elements. This leads to advantages in terms of speed and reduced efforts for alignment when the method according to the invention is implemented and represents a considerable advantage compared to the state of the art.

In the case of time-sequential operation, either light source (19) or light source (23) emits light, where recording of the image of the sample using detection unit (11) is synchronised with it.

In a further representation of the invention both the light distributions or illumination patterns, respectively, are emitted at the same time. For encoding of both the distributions the polarisation or the spectral composition of the light emitted can be used. For this purpose, both the optional polarisation filters or spectral filters (20) and (24), respectively, are used (see FIG. 2). In case of polarisation filters these are crossed with respect to each other, such that the light emitted in direction (22), which passed filter (20) or (24), respectively, has two directions of polarisation that are orthogonal with respect to each other. As an alternative to linearly polarised light, left or right circularly polarised light can be used.

The time simultaneous emission of two illumination patterns that are encoded via polarisation or spectral characteristics as in the mentioned embodiment of the invention has further advantages in terms of speed and allows the generation of optical section images in real-time, as it is desirable especially for material microscopy in reflection mode as well as for the construction of surface measurement systems for microscopic or macroscopic objects.

Figure 2B:
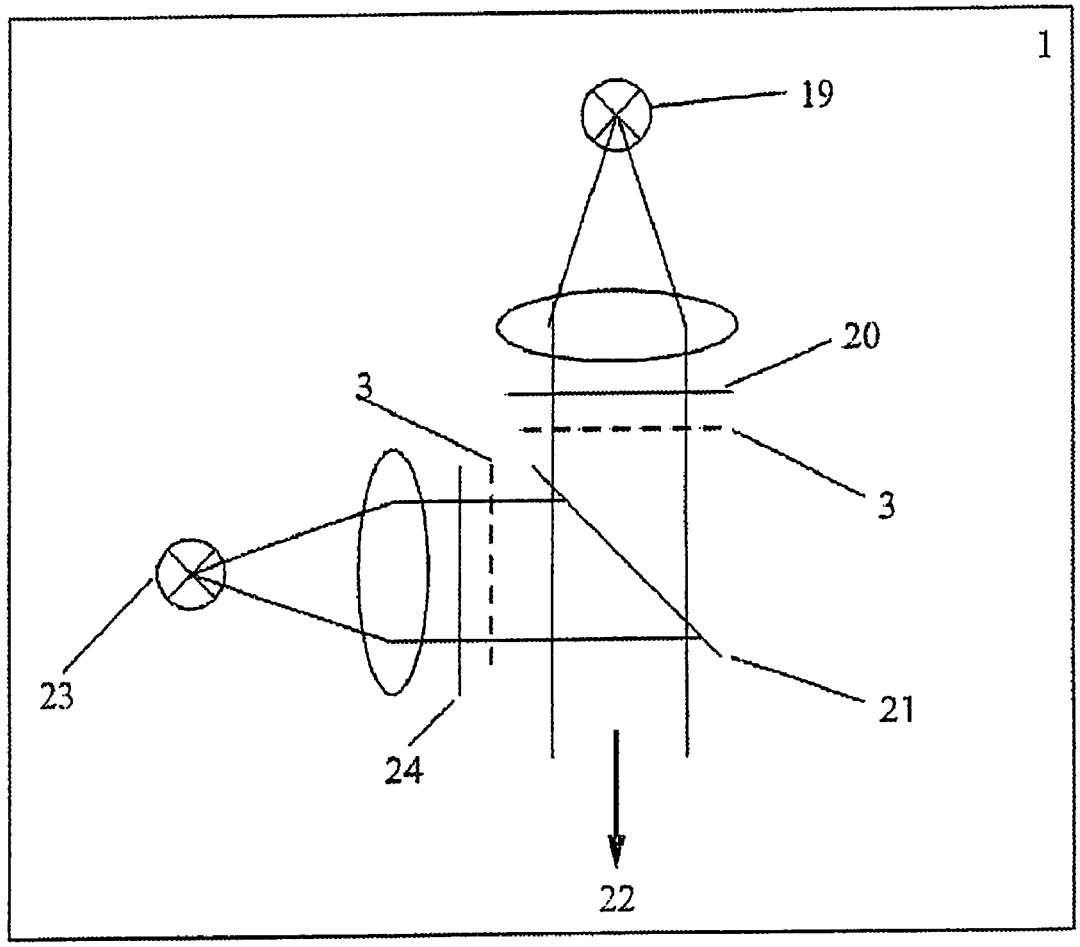
FIG. 2b is a block diagram which shows an alternate arrangement of the illumination unit formed in accordance with the present invention.

A further option for the implementation of an illumination unit according to the invention is shown in FIG. 2b), where the same labelling conventions are used as in FIG. 2. Here two masks are arranged, both located in planes (3) conjugated with respect to each other. Both masks are operated in transmitted light. The arrangement shown here has a slightly higher optical efficiency compared to FIG. 2, but it also requires the alignment of the two masks with respect to each other, such that, depending on the selection of the light source, two illumination patterns are emitted in direction (22), where their individual phase is shifted by 180 degrees with respect to each other. This alignment has to be done only once and is not problematic, since only alignment of beam splitter (21) is required, which causes negligible distortions of the image.

Figure 3:
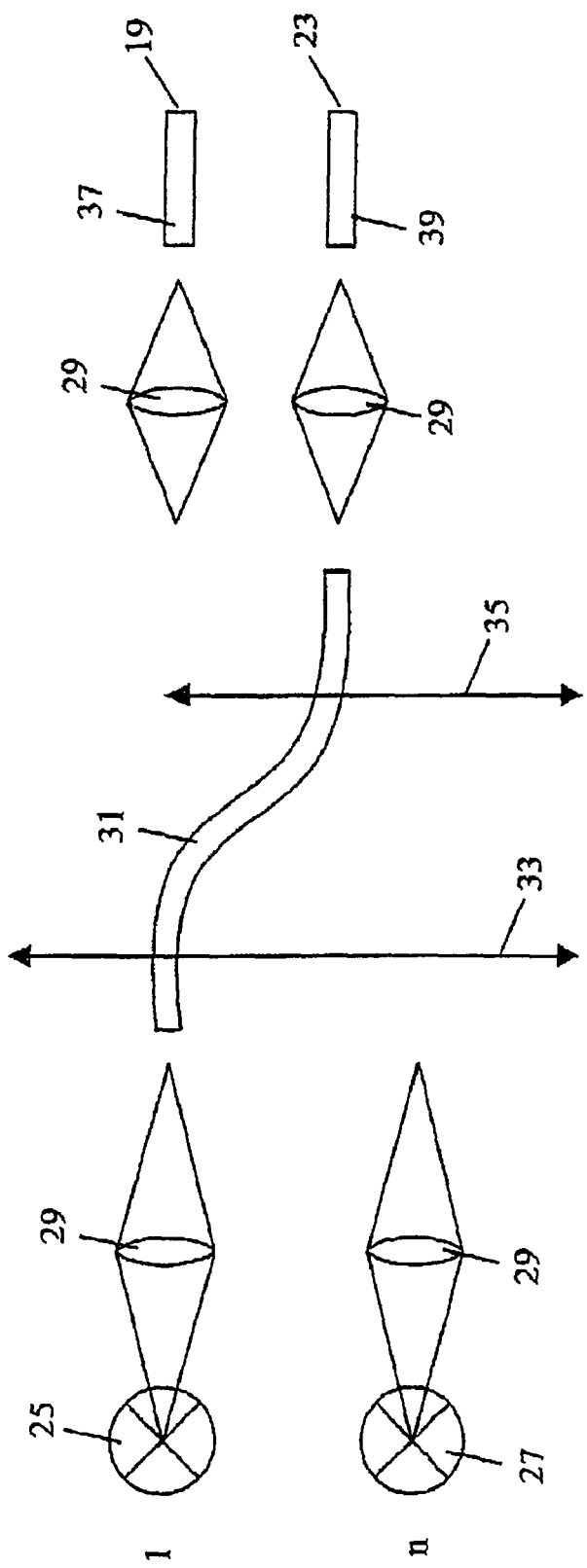
FIG. 3 is a block diagram which shows an advantageous arrangement for the implementation of the light sources of the illumination unit formed in accordance with the present invention.

FIG. 3 shows an advantageous arrangement according to the invention for the implementation of the light sources (19) and (23). Here the light sources (19) and (23), which are part of the illumination unit (1), are replaced by the output of two optical fibres or light guides (37) and (39). The arrangement further contains a number of n light sources, where in FIG. 3 only light source 1 (25) and light source n (27) are shown. These light sources can also represent different spectral components of the light, which was created by a single source and then spatially and spectrally separated. The different light sources may have different spectral compositions. An optical fibre (31) is connected to the actuators (33) and (35) and uses the optical units (29) for coupling.

According to the invention the overall arrangement works as a switch, allowing connection of any light source with one of the two outputs (19) or (23) of the optical fibre. This has two main advantages: first, only one item of a light source is used, which reduces cost and guarantees the same spectral composition in both the projection steps. Second, the outputs (19) and (23) can operated as point light sources with fixed alignment, which remains aligned with respect to the remaining optics of the projection unit. This reduces the effort required for alignment.

Figure 4:
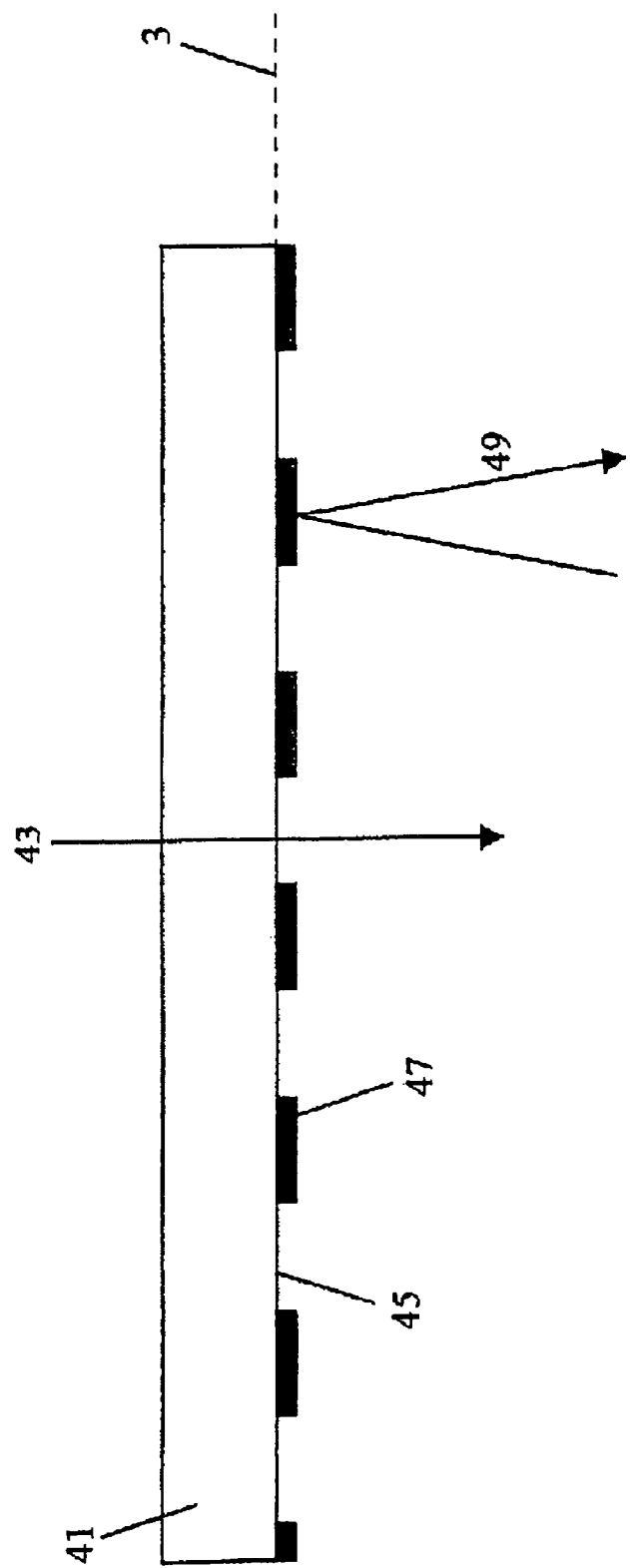
FIG. 4 is a view showing an example of a mask formed in accordance with the present invention.

In FIG. 4 an example design for a mask is shown, which can be part of the projection unit shown in FIG. 2 and is located in plane (3). In the simplest case, there are homogenous areas (47) with high reflectivity and low transparency as well as homogenous areas (49) with high transparency and low reflectivity arranged on a transparent substrate (41) in an alternating fashion. Here the total combined areas of the transparent and the intransparent regions, respectively, have the same size. Even though a binary pattern was used for this example, mask designs with several levels of transmission and reflection or continuous distributions are feasible.

Figure 5:
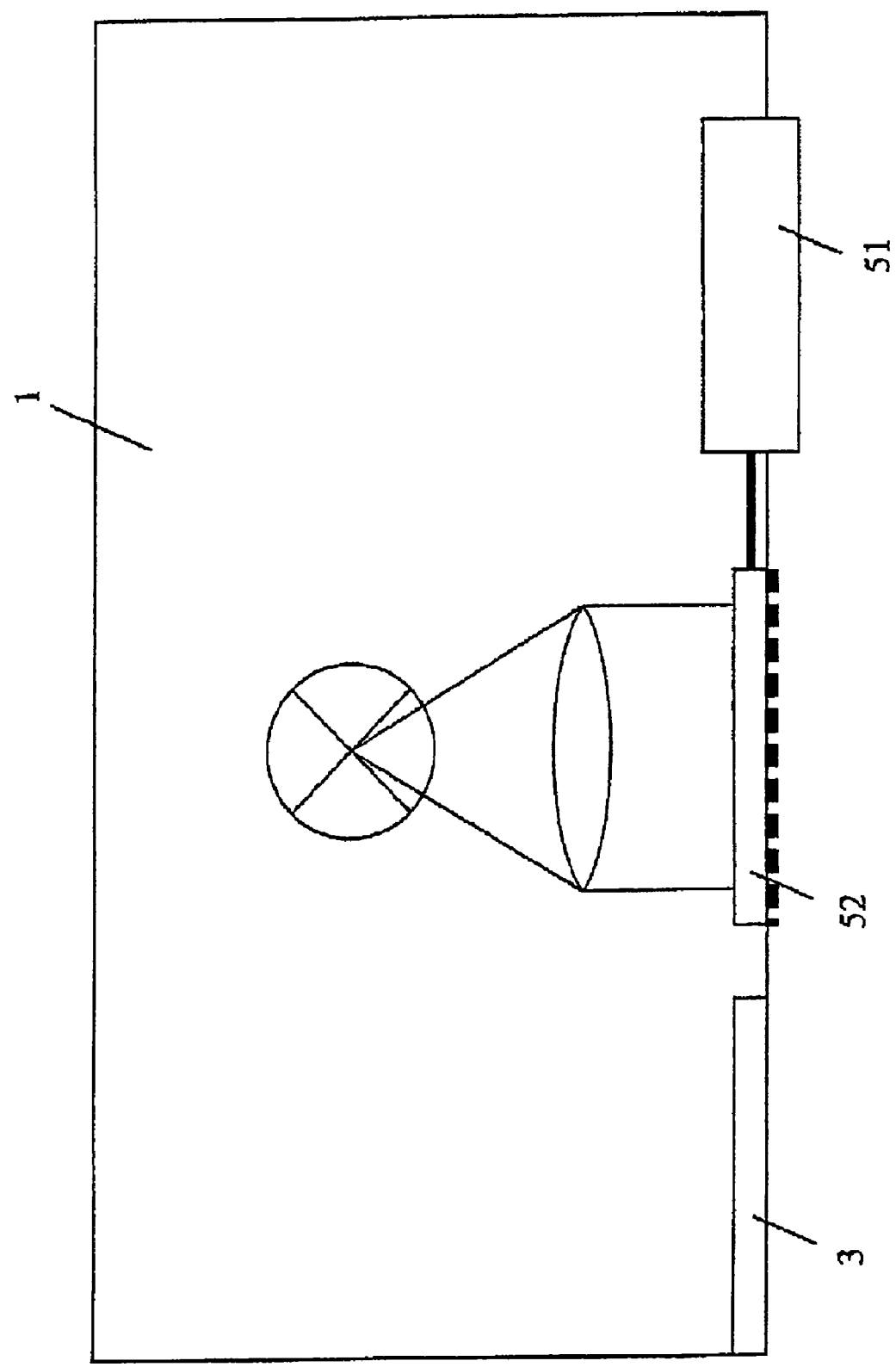
FIG. 5 is a block diagram showing an arrangement for an illumination unit.

In FIG. 5 there is shown an arrangement for an illumination unit (1) according to the state of the art described in Reference No. 2, where a mask (52) is operated in transmitted light and moved by an actuator (51) in a direction perpendicular to the optic axis. Such an arrangement can also be used for an implementation of the method for the generation of optical section images from two projection steps according to the invention. Compared to the state of the art using three projection steps, this allows increased speed of the sample scan process and reduced photo-bleaching. As opposed to the implementation with fixed mask according to the invention in FIG. 2, this requires the actuator (51), which is required to deliver a good repeatability for the setting of both the light patterns projected.

Figure 6:
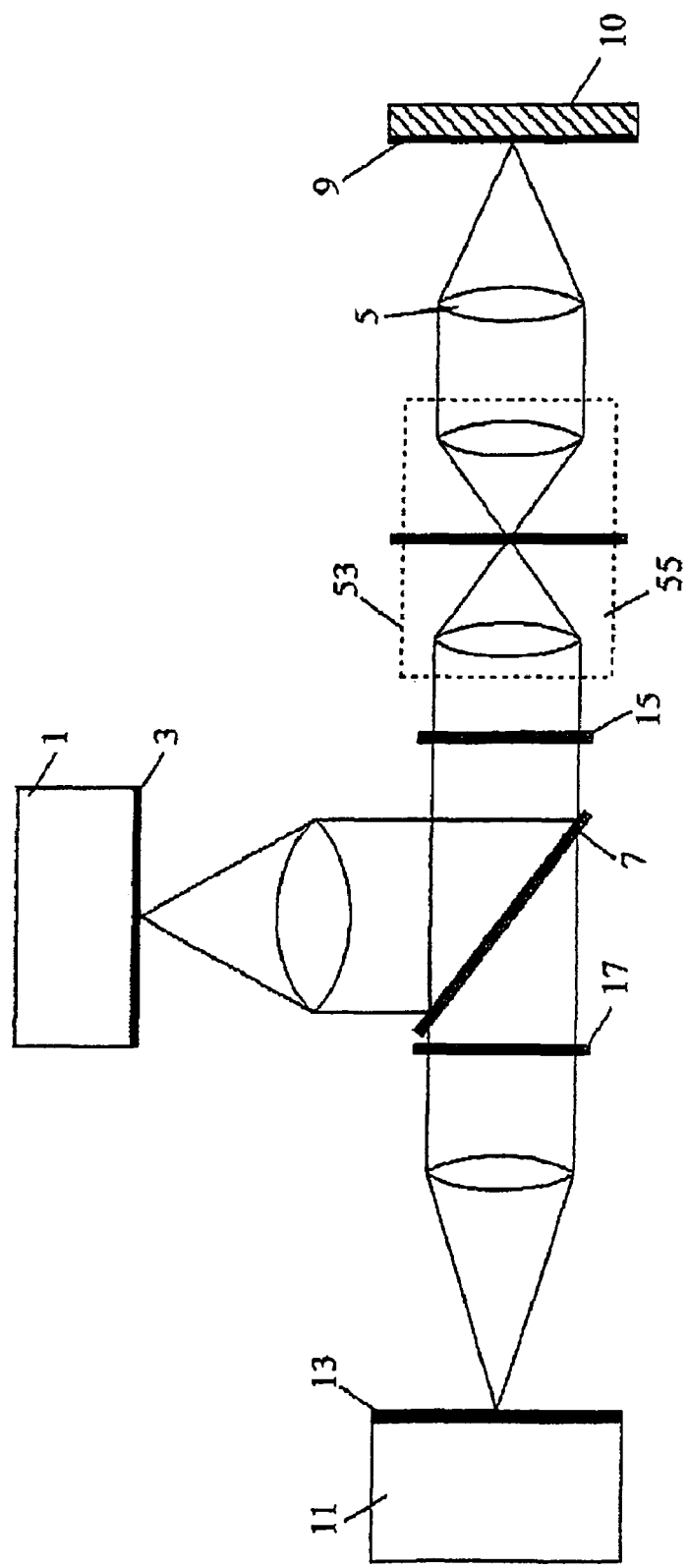
FIG. 6 is a block diagram which shows a arrangement having an additional intermediate optics for the implementation of the method of the present invention.

In FIG. 6 aspects of the calibration measurement and of the chromatic correction are discussed. Here the diagrammatic representation of FIG. 1 is supplemented by an additional intermediate optics (55). For a calibration measurement, depending on the requirements, a fluorescing and/or reflecting and/or scattering element (53) can be swivelled into the beam path. The plane of the element (53) corresponds to an intermediate image plane and is conjugated with respect to (3), (9) and (13). The location and properties of the intermediate image and the intermediate image that is formed when a flat sample is re-imaged back into the plane of the element (53), can be identical. For that reason, swivelling element (53) into the beam path can be identical to mounting a calibration object in front of the objective (5). Swivelling of element (53) into the beam path may be performed automatically and internal to the optical arrangement. This simplifies the use and allows a fully automated calibration measurement, e.g. recording of data for the subsequent determination of the local phase $\alpha(x,y)$ and optionally the local grating frequency $g(x,y)$ for every location within the detector coordinate system (x,y), using a known calibration object. In addition, this object cannot get contaminated or lost since it is part of the optical arrangement. The element (53) can be a diffusely reflecting or fluorescing object or may have a surface reflecting at a certain wavelength only. A calibration measurement can be performed at any time, independent of element (53), with the help of a calibration object that is manually placed in the sample space in front of objective (5).

A further problem of arrangements according to the state of the art is a change in intensity during the projection. Especially high pressure mercury lamps can have fluctuations of the light intensity due to their design, which can lead to artefacts in the process of structured illumination. This can be compensated, if the relative illumination dose of the different projection steps is measured in conjunction with the image acquisition at the detector (11). This information on the relative illumination intensities can then be used in the calculation of the optical section image and can contribute to the reduction of artefacts. For the measurement of the relative illumination doses, the illumination pattern, located at (3) or imaged to that location, can contain test areas at the edge of every projected structure. According to the invention, an element, which can also be at the calibration element (53), is only partially inserted into the beam path at the location of an intermediate image of the projected pattern, e.g. location of (53), such that it is imaged onto the detector (11) only at the edge of the field of view. This element remains in the beam path during the whole projection procedure for the generation of optical section images. This allows logging of the relative intensities of the projection steps on the detector (11) independent of the sample observed and its properties.

Another issue related to arrangements according to the state of the art and an obstacle, when higher system speeds should be achieved, occurs when imaging with several wavelengths is performed, especially in fluorescence microscopy. Due to chromatic aberration, especially axial chromatic aberration, the planes (3) and (13) in FIG. 6 are not exactly conjugated with respect to each other any more. Arrangements according to the state of the art described in Reference Nos. 3-5 solved this problem by re-focussing the mask, corresponding to an axial shift of the plane (3) in FIG. 6. For this purpose, there are often long distances required, leading to overall long process times when using several wavelengths. Especially for fluorescence microscopy, the simultaneous recording or at least the recording of images in fast succession is often required.

According to the invention, this task is solved by means of spectral correction, without movement of the structure or mask being projected. Therefore, optional correction elements are inserted in planes (15) and/or (17) and as an option in the detection unit (11) (see FIG. 6). These correction elements can for example consist of lenses with well known dispersion properties or diffractive optical elements or holograms, that influence the spectral properties of the optics. Diffractive optical correction elements can be fabricated especially for the correction of a certain optical configuration. When the objective is changed, a change of the correction elements may also be necessary.

Figure 10:
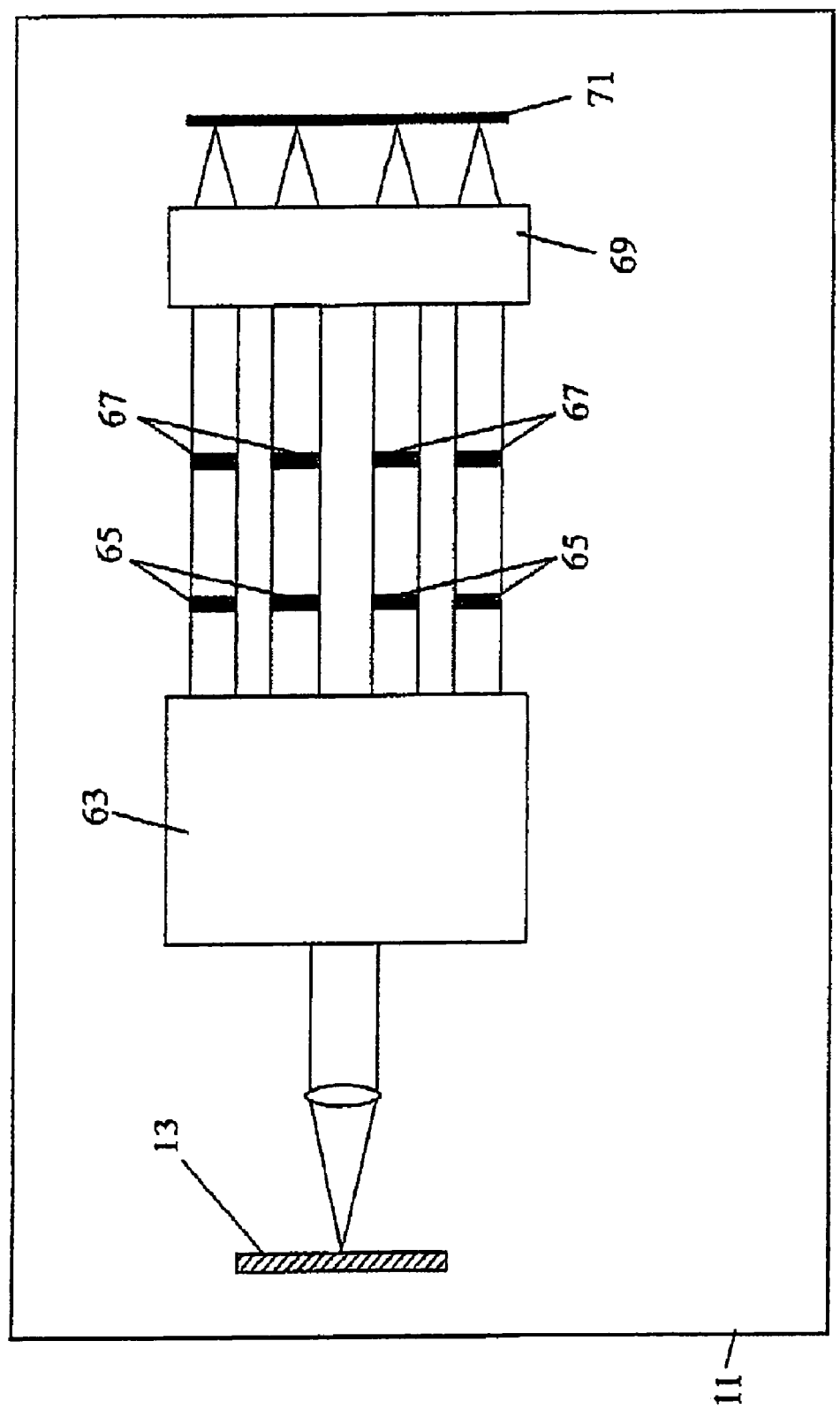
FIG. 10 is a block diagram which shows a modification to the optical arrangements formed in accordance with the present invention.

Additional measures for correction within the detection unit (11) that may be necessary, are discussed with the help of FIG. 10 further down. It is advantageous, if the correction elements (15) and (17) are located in a part of the beam path that is essentially collimated. Here the correction of the axial chromatic aberration can be implemented in two different ways, where both designs can avoid an axial movement of the structure projected.

In the first version of partial chromatic correction, the correction elements make sure that the planes (3) and (13) are conjugated with respect to each other for all wavelengths used for imaging. Despite the fact that planes (3) and (13) remain conjugated with respect to each other, such a correction may lead to a wavelength dependence of the axial position of the illumination pattern in or on the sample (10). This may be easily compensated for by using software. During the process of physical axial scanning of the sample the slightly displaced axial locations of the projection can be taken into account and assigned when the 3D dataset of the sample is built up. As an alternative to that, the sample itself may be displaced by the amount of the axial displacement during the change of the wavelength. In most microscope systems this can be accomplished faster on the side of the sample than the axial movement of the structure (mask or DMD) on the illumination side.

For the second version, the complete axial chromatic correction ensures that the planes (3) of the projected structure, (9) in or on the sample as well as (13) on the detector are conjugated with respect to each other for all wavelengths used.

Figure 7:
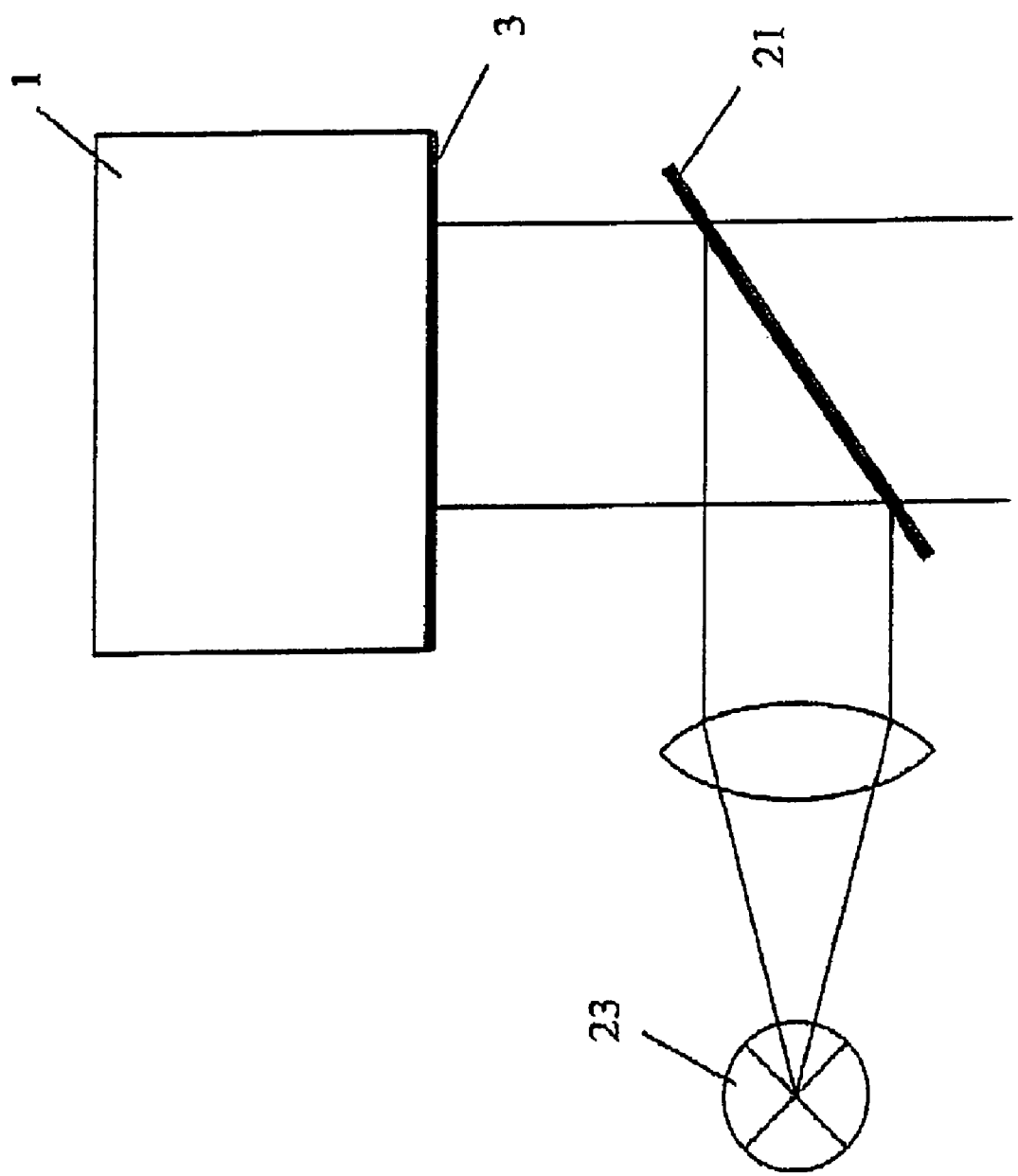
FIG. 7 is a block diagram which shows a arrangement having a digital mirror device for the implementation of the method of the present invention.

FIG. 7 shows a further implementation of the illumination unit (1) according to the invention. Here in plane (3) there is a DMD chip located (digital mirror device, also known as DLP technology from Texas Instruments). The light source (23) illuminates the DMD chip via the beam splitter (21). The illumination pattern to be projected, which is displayed on the chip, is now emitted through the element (21). Instead of the DMD chip, there are also LCD modules feasible, which are mounted in plane (3) and can be operated in transmitted light using the light source (19) shown in FIG. 2. Such an arrangement has the advantage, that the pattern to be projected can be updated very quickly by using software. An adjustment of the pattern projected can be easily and quickly accomplished, as it may be necessary when an objective lens is changed.

Figure 8:
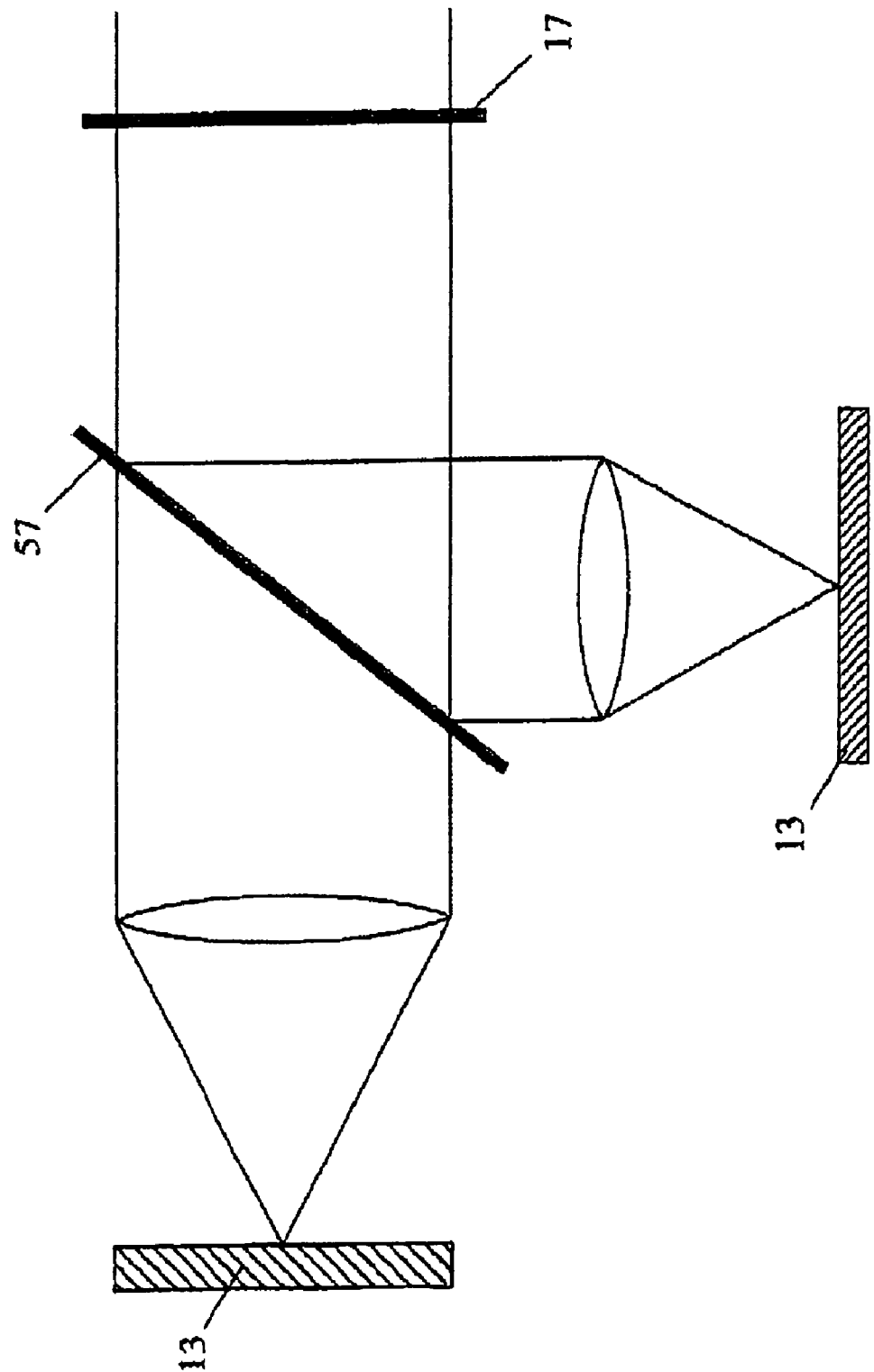
FIG. 8 is a block diagram which shows the implementation of the detection unit formed in accordance with the present invention.

FIG. 8 shows an example for the implementation of the detection unit (11) according to the invention. Here the incoming light is splitted via a beam splitter (57) and dispatched onto two spatially resolving detectors (for example CCD's), which are located in the two conjugated planes (13). For example, the beam splitter (57) can be a dichroic mirror or a polarisation dependent beam splitter. Therefore, two spectral regions or states of polarisation of the image can be observed simultaneously and separately. If the two light patterns projected are encoded spectrally or via polarisation according to FIG. 2, projection and recording of both the illumination patterns can be done simultaneously and in real-time. This principle allows construction of considerably faster designs for the measurement of surface properties according to the method of the invention, compared to previous state of the art designs described in Reference Nos. 2-6.

Figure 9:
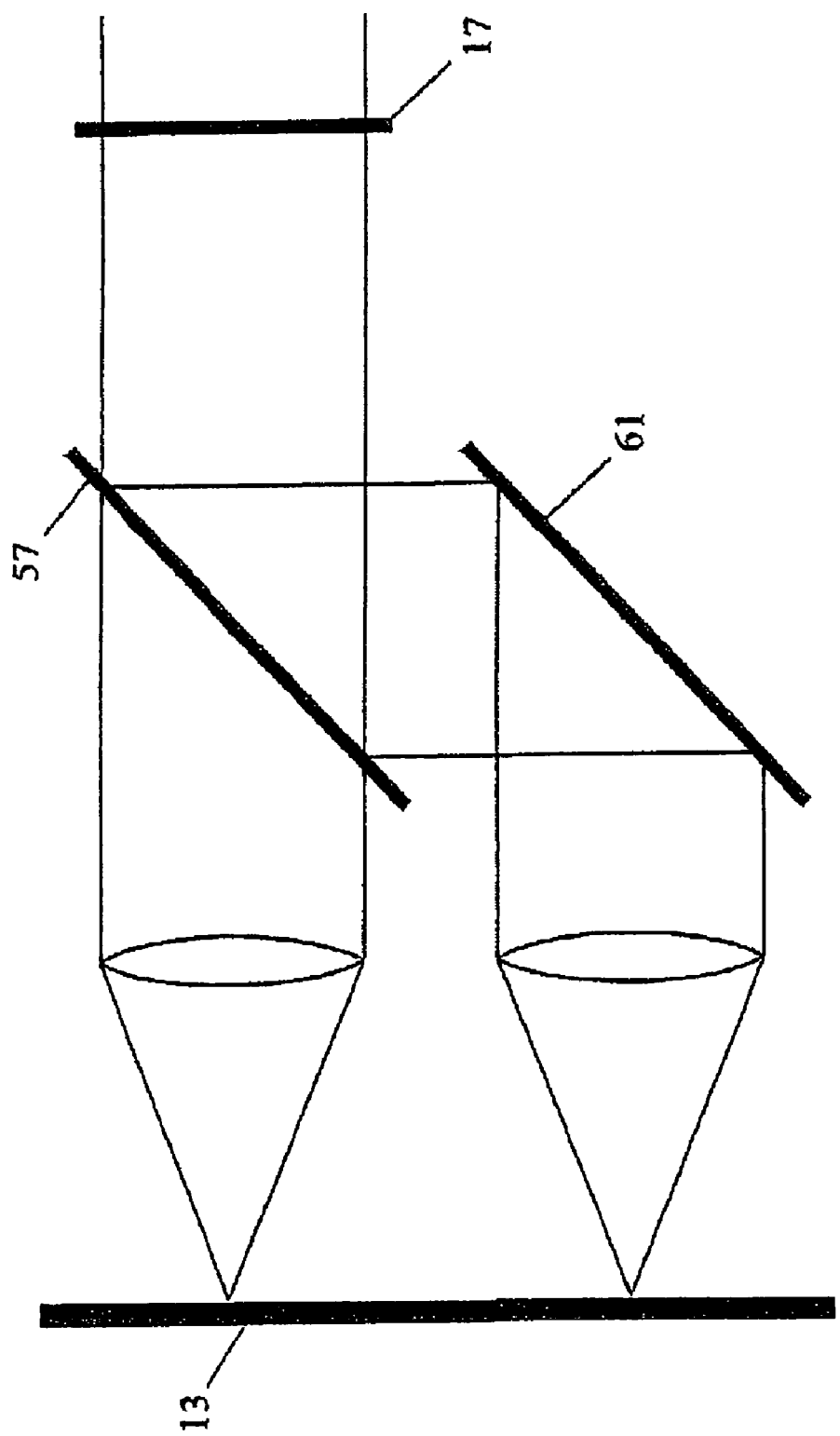
FIG. 9 is a block diagram which shows the implementation of an alternative detection unit having a beam splitter and full mirror.

FIG. 9 shows a further possibility for the implementation of the detection unit (11), where a beam splitter (59) and a full mirror (61) are used. The beam splitter (59) can be a dichroic mirror or a polarisation-dependent beam splitter. The parallel detection is similar to the implementation displayed in FIG. 8. However, the parallel observation is accomplished with a single detector located in plane (13), which saves cost at the expense of reduced resolution.

FIG. 10 discusses the modification of existing optical arrangements according to the invention, where simultaneous generation of optical section images in different spectral channels is feasible, without an axial movement of the light distribution projected (e.g. mask). This measure can be applied in conjunction with or without the spectral correction elements (15) and (17) discussed in FIG. 6. According to the state of the art there are arrangements that split the image of an object in different channels (such as spectral or state of polarisation) and simultaneously form an image of these channels next to each other on a spatially resolving detector, for example a CCD chip, such as described in U.S. Pat. No. 5,926,283, entitled "Multi-spectral Two Dimensional Imaging Spectrometer", which issued to Mark Hopkins (hereinafter referred to as Reference No. 10). In the presence of axial chromatic aberration the axial position of the entering intermediate image (13) can depend on wavelength. The optical unit (63) splits the image depending on its spectral characteristics into several channels, where four channels are displayed here. Subsequently, in parts of the layout where the beam is essentially collimated, the individual channels may contain spectral filters (65) according to the state of the art. The optical unit (69) is focussing the parallel channels in such a way, that they are imaged next to each other onto a spatially resolving detector (71). In FIG. 10, four channels are arranged linearly next to each other, another common configuration would also be the projection into four different quadrants of the detector. According to the invention, this arrangement is modified by the use correction elements (67), which are preferably located in the collimated part of the beam path and preferably positioned after the spectral filters (65). The correction elements (67) may form combined units with the respective filters (65). The correction elements are preferably diffractive optical elements. This correction makes sure that, despite of the wavelength dependence of the axial locations of the intermediate input image (13), all spectral channels are focussed simultaneously and in parallel onto the detector (71). The diffractive optical elements or holograms (67) may also be arranged next to each other on the same substrate.

By means of the combination of the simultaneous detection of different spectral channels according to the invention without moving mechanical parts and the method and arrangement for the generation of optical section images from two illumination steps and without moving mechanical parts according to the invention, one can design optical systems with depth discrimination and high optical efficiency, which operate considerably faster and can be constructed at lower cost, compared to the state of the art.

Because the spectral correction of the different spectral imaging channels is an important aspect of structured illumination systems according to the state of the art and represents an obstacle for an increase in speed for the scanning with several wavelengths, a further solution for the spectral correction in a structured illumination system according to the invention will be disclosed in the following.

It is the aim for a spectral correction arrangement to achieve matching of the focal plane of the illumination pattern created in the sample with the focal plane conjugated with the detector for different wavelengths.

Figure 11A:
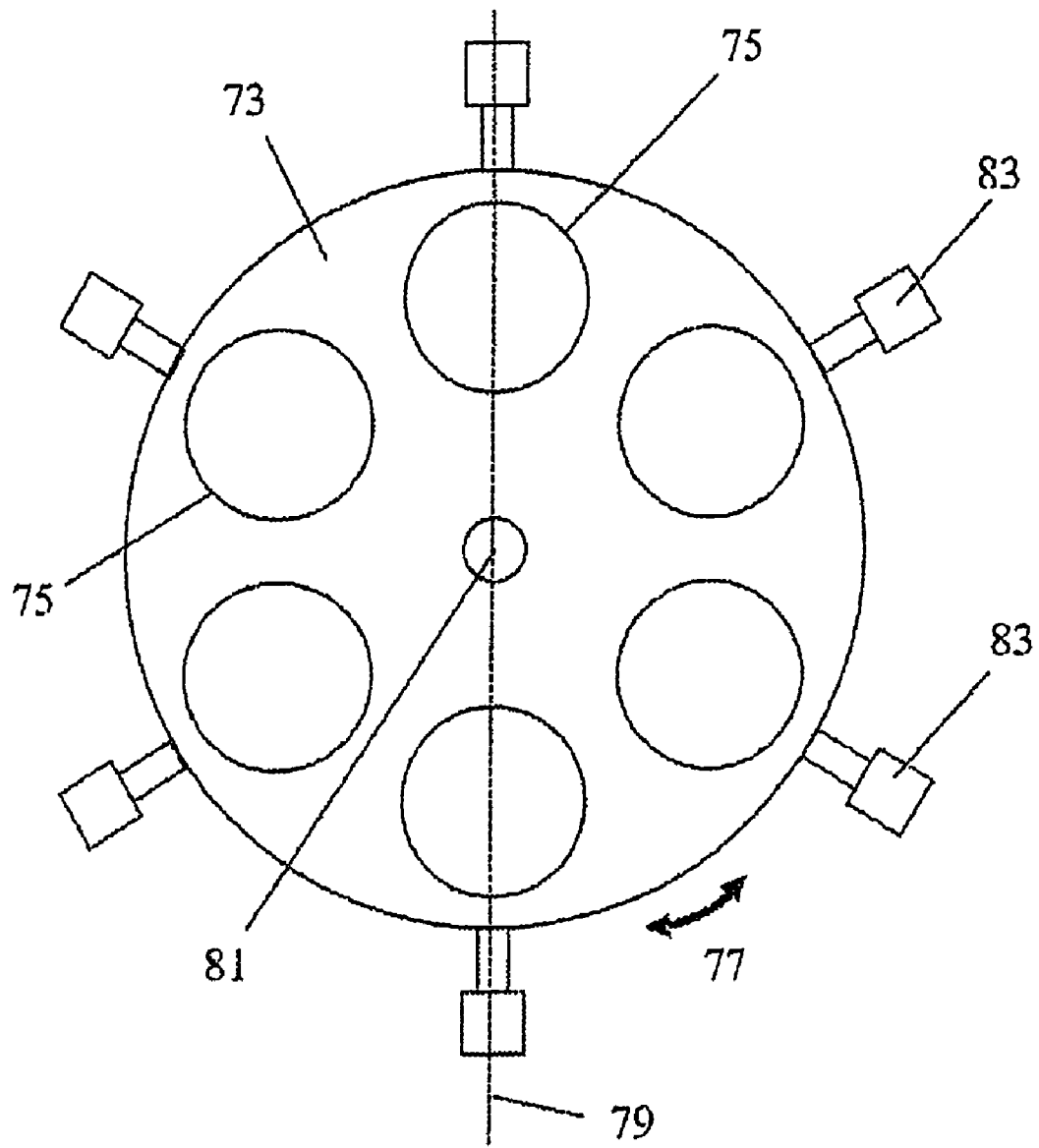
FIG. 11a is a first view of a component changer in the form of a component wheel formed in accordancce with the present invention.

Due to the spectral properties of the optics, e.g. differences in the spectral properties if the optical pathways for illumination and detection, the axial position of the illumination pattern projected into the sample may, depending on the wavelength, differ from the axial position of the plane imaged onto the detector. Therefore, planes (3) and (13) (see FIG. 1) would not be conjugated with respect to each other, as demanded. The task of spectral correction is therefore to ensure conjugation of planes (3) and (13). This may for example be accomplished by an axial positioning of the illumination pattern or by an appropriate displacement of the tube lens. As an alternative to that, the spectral properties of the optics can be corrected as described in the previous embodiment of the invention, such that plane (3) from FIG. 1) is conjugated with plane (13), independent from the wavelength. According to the state of the art, the chromatic correction is implemented via an axial movement of the structure projected (grating) by means of a stepper motor. Furthermore, the grating has to be changed manually in order to adjust the setting respective grating period for different imaging conditions. In the following there will be an arrangement according to the invention disclosed where the problem of the chromatic correction at increased speed as well as a change of the illumination pattern (e.g. grating) is solved. An embodiment of the invention is shown in FIGS. 11a-11c.

The periodic illumination pattern projected into or onto the sample is preferably in the form of a mask and can be swivelled into the beam path by means of a component changer. The mask is in an axial location that is conjugated with plane (3) (see FIG. 1). Here the component changer is in the form of a component wheel (73), linear arrangements are also feasible. FIG. 11a shows a plane perpendicular to the optic axis, FIG. 11b depicts a cross section through the axis of rotation (81) of the component wheel (73) in a plane (79) parallel with respect to the optical axis. The component wheel (73) has several component slots (75) for optical components, which can be swivelled into the beam path or exchanged by a rotation (77) of the wheel. It is advantageous, if the individual positions of the component wheel are defined by appropriate lock-in positions. FIG. 11a shows an example with 6 component slots (75) sketched, but the number of slots can be matched to the requirements. According to the invention, the component wheel (73) is designed such that the axial position of the optical components (87) located in it may be aligned in axial direction (8.5).

Figure 11B:
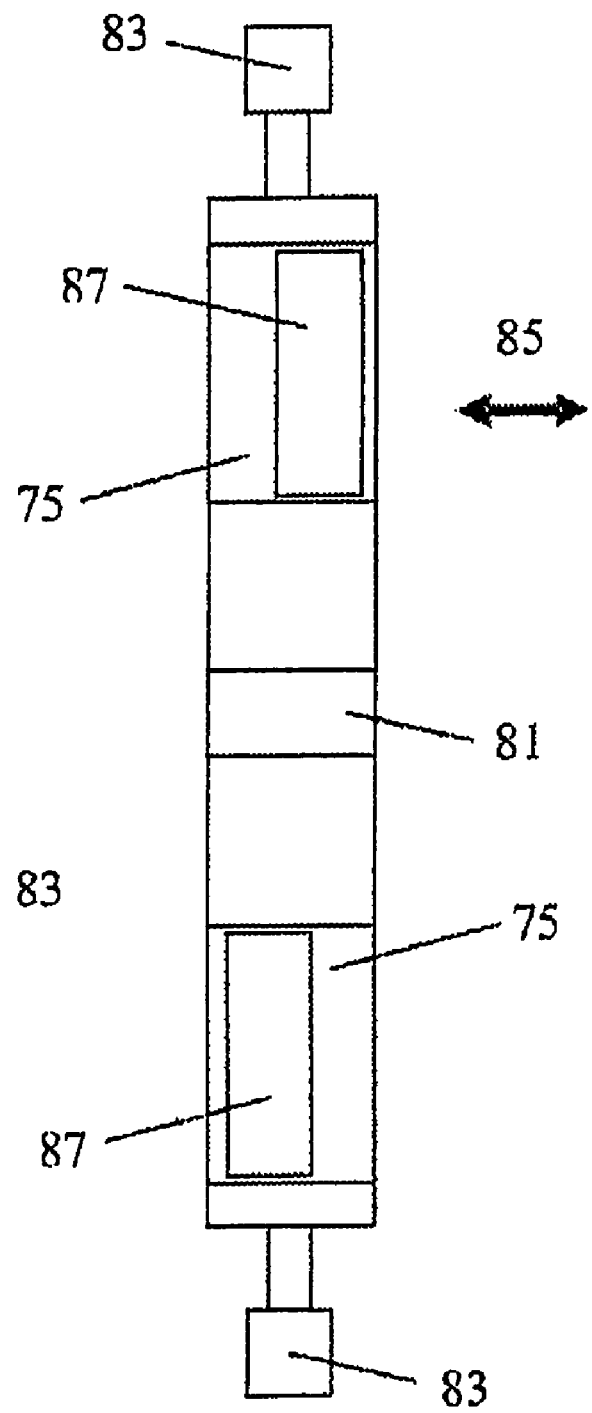
FIG. 11b is a cross-sectional view of the component changer formed in accordancce with the present invention.
Figure 11C:
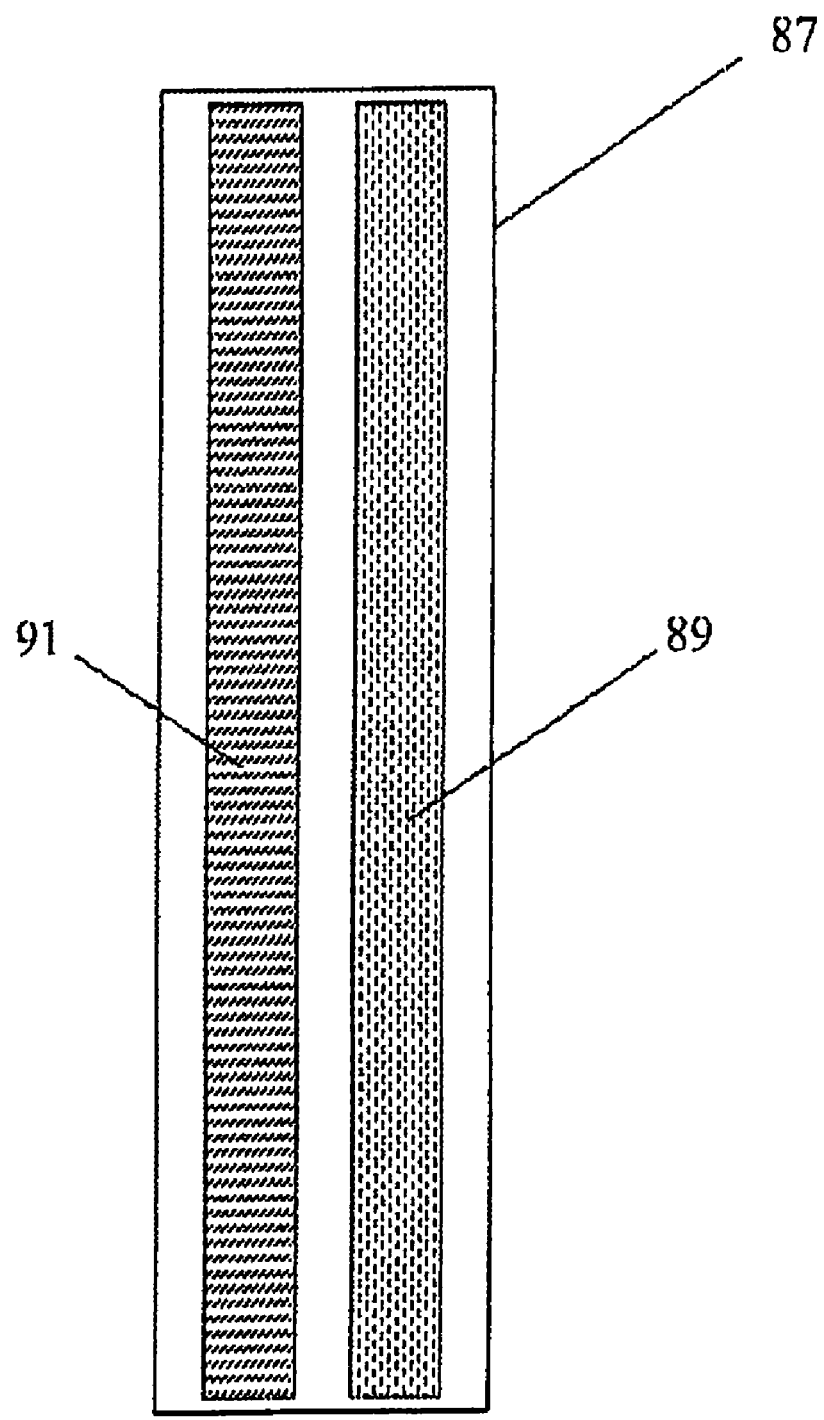
FIG. 11c is an enlarged view of the optical components, including a spectral filter, and a structure to be projected.

In the cross section of FIG. 11b there are two optical components (87) shown that are located in different axial positions. The adjustment of the optical components (87) in axial direction (85) can be done manually or by means of electric actuators. FIG. 11 shows an embodiment with manual adjustment knobs (83) for the alignment in axial direction. A key feature is here that the change between components of the component wheel (73) can be fast. Times of approximately 50 milliseconds can be achieved. A direct axial positioning of the structure projected by means of a stepper motor according to the state of the art could achieve this with great effort only. The arrangement disclosed here results in an advantage in terms of speed since one can change very rapidly between pre-aligned axial positions of the different components (87), while the actual axial alignment is done manually or with slow and inexpensive actuators.

According to the invention, the wheel can carry masks with different pattern sizes. When a component slot (75) is empty, this enables switching from the mode of structured illumination to the additional conventional mode. The optical components (87) held in the component slots (75) can be premounted units, consisting of a spectral filter (91) and a structure to be projected (89) (see larger display in FIG. 11c). Here element (89), used to produce an illumination pattern at the location of the sample, can be a mask where transmission and/or reflection and/or phase properties were patterned, such that a periodicity in at least one spatial direction exists. One or more field stop diaphragms (iris or fixed diameter) can also be mounted in the component slots (75) or in the individual components (79), respectively.

The arrangement described and depicted in FIG. 11 can fulfil several tasks at the same time:

A change of the component wheel (73) position can, depending on the components installed, switch between several axial alignments of the optical components (87), which corresponds to the chromatic correction of the arrangement; one can change between different pattern sizes of the masks, appropriate spectral filters can be swivelled into the beam path that are matched to the corresponding chromatic correction (axial position) and the arrangement can be switched from the mode of structured illumination into the conventional illumination mode.

Figure 12:
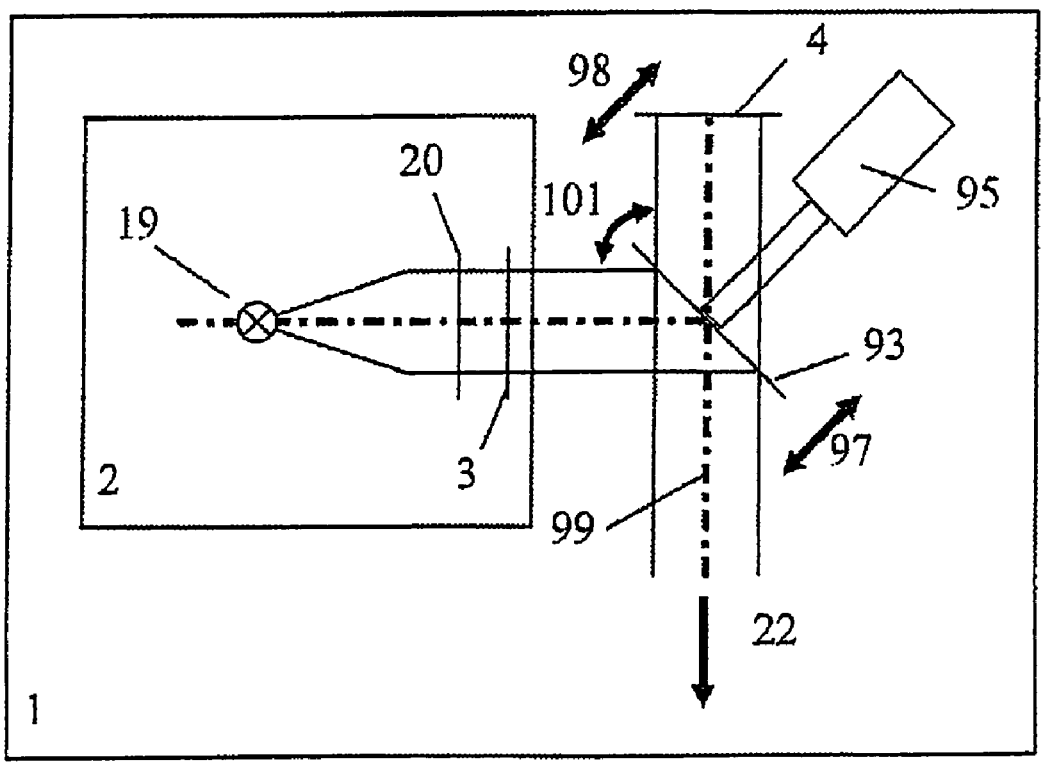
FIG. 12 is a block diagram which shows an illumination unit which provides illumination distributions with different phase settings for the projection into or onto a sample.

An additional illumination unit (1) for the implementation of structured illumination is depicted in FIG. 12. It is the task of this illumination unit (1), which was also previously described in different embodiments, to provide illumination distributions with different phase settings for the projection into or onto the sample. As a special feature of the embodiment shown in FIG. 12 the phase shifting of the illumination structure created in the sample as well as the spectral correction of the arrangement is done by means of a single actuator. The element for the generation of an illumination distribution within the sample is located in plane (3) previously described, which is conjugated with the object plane (9) and the intermediate image plane respective detector plane (13). The exact configuration of the optical system, for which the planes (3), (9) and (13) are conjugated with respect to each other, may depend on the wavelength. Fulfilment of this condition (conjugated planes) for different wavelengths is the task of the chromatic correction. The arrangement uses a light source (19), which may be switched spectrally. The phase shift of the illumination pattern projected into or onto the sample is realised by a mirror (93). In FIG. 12 the optical axis (99) has an inclination of 45 degrees with respect to the mirror, however, other angles can also be chosen. The mirror (93) is moved by means of an actuator that may be based on piezo technology. The mirror is moved linearly (97) or tilted (101).

Tilting (101) gives control of the phase of the pattern projected while a linear movement (97) allows controlling the phase as well as the adjustment of the chromatic correction, as will be discussed in the following. A linear motion of the mirror (93) causes a movement (98) of the image (4) of the fixed pattern in plane (3), which is projected into or onto the sample. The motion (98) of the image (4) has two components: an axial and a lateral (perpendicular to the optical axis (99)). The lateral component of the motion affects the phase position of the illumination pattern in/on the sample, the axial component of the motion affects the spectral correction. The optics for the further imaging of the illumination pattern, which may have the form of a tube lens, typically features a small numerical aperture and thus a corresponding large depth of focus. Therefore, the arrangement can be configured such that the phase position of the illumination pattern is more sensitive to a movement (98) than the chromatic correction (axial position of (4)).

For a small movement of (97) in the order of the periodicity of the pattern in plane (3) imaged, primarily the phase of the light distribution projected into or onto the sample is changed while the effect of the axial motion component of (98) can be neglected. If the actuator (95) is moved over a larger distance, apart from the change in phase of several periods of the projected pattern, the axial position of the image of the structure is changed, which can be used for the spectral correction of the arrangement. A single actuator (95) is therefore sufficient to control the phase of the pattern projected as well as the axial position of the illumination pattern in the sample. This is essentially feasible due to different sensitivities of both parameters, influenced by a single actuator.

This arrangement according to the invention can be used in conjunction with the method of structured illumination with only two illumination steps according to the invention or in conjunction with methods of structured illumination with three or more steps according to the state of the art.

The illumination unit (2) also displayed in FIG. 12 is a sub-unit of the illumination unit (1). It uses the masks in plane (3) as mentioned to create an illumination distribution. In contrast to the illumination unit (1) described in several embodiments, the unit (2) creates only a single, steady illumination distribution and does not feature the option to manipulate the phase of the illumination distribution, as arrangement (1) does.

In the following, further embodiments for a realisation of the present invention or another method of structured illumination according to the state of the art will be given, where the simple integration into existing microscope systems as well as the problem of the axial chromatic correction is considered primarily.

For now, FIG. 1 is referred to again. The reason for drifting apart of the plane imaged by the detection unit (11) within the sample (10) and the plane conjugated with plane (3) during a change of wavelength can be the different wavelength dependent properties of illumination optics (103) and imaging optics (104). This problem can be solved by means of an axial re-adjustment of the mask used for the generation of the illumination distribution.

According to the invention, the required efforts for the spectral correction can be reduced or avoided altogether, if optics (103) for imaging of the illumination pattern into the sample (illumination tube optics) as well as the optics (104) for imaging of the illumination distribution from the sample onto the detection unit (detector tube optics) have identical properties, i.e. are designed identically. In a standard microscope, which was not designed for structured illumination, illumination tube optics and detector tube optics often have different properties and dimensions, since they were designed for different requirements.

Figure 13:
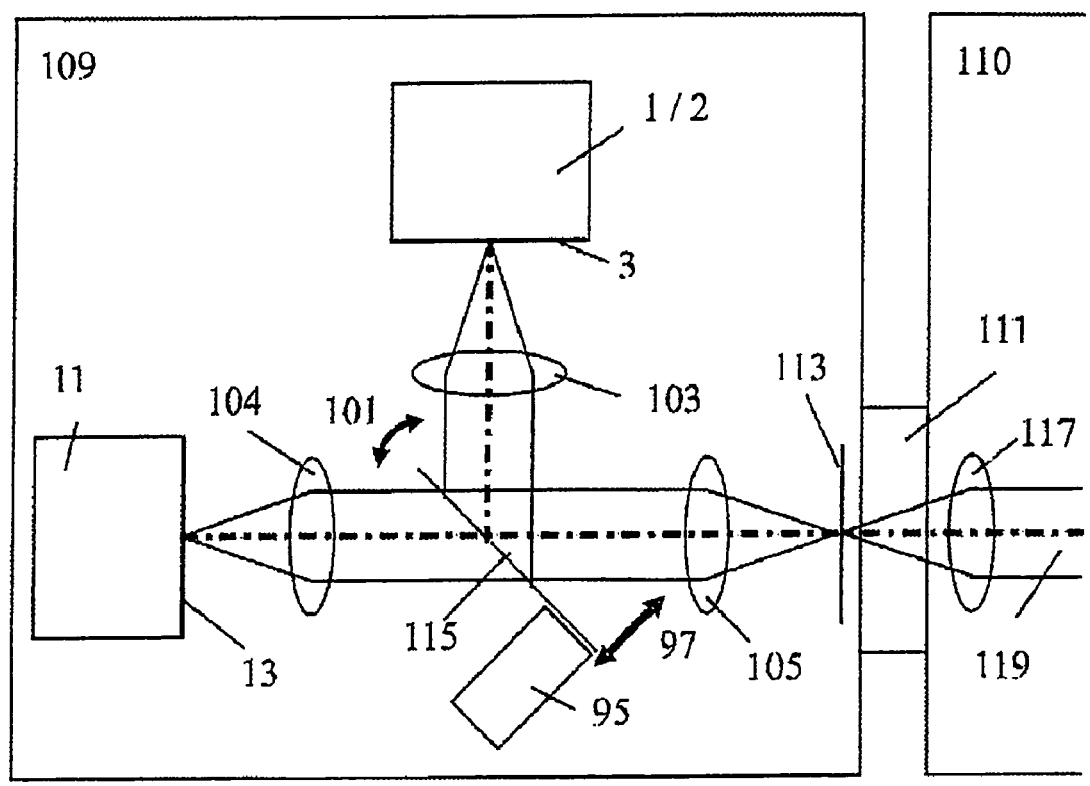
FIG. 13 is a block diagram showing an upgrade unit attached to a camera port of a microscope.

In FIG. 13 an upgrade unit for implementing the structured illumination in a microscope is shown, where the upgrade unit (109) is attached to the camera port (111) of the original microscope (110). Such a camera port is a standardised mechanical interface for mounting a spatially resolving detector, such as a CCD camera. A common standard is "C-mount". The intermediate image plane (113) corresponds to the plane where the image sensor (e.g. CCD) was supposed to be located in the original microscope arrangement (110). In FIG. 1, the detector plane (13) corresponds to the intermediate image plane (113) from FIG. 13.

One could upgrade the microscope arrangement shown in FIG. 1 by removing the detection unit (11), the dichroic mirror (7) and optionally other illumination means, where the upgrade module from FIG. 13 is attached such that the intermediate image plane (113) is located in the position of the former detector plane (13) of FIG. 1. For the change of the phase of the illumination pattern projected there are two possibilities or configurations, respectively, that are both contained within FIG. 13.

The first configuration uses the illumination unit (1) described containing arrangements for the change of the phase setting in combination with a fixed, dichroic or semi-transparent mirror (115). The second configuration uses the less complex illumination unit (2), which emits a static illumination distribution and manipulates the illumination pattern projected onto or into the sample by means of an actuator (95), which moves the dichroic or semi-transparent mirror (115) in order to change the phase of the illumination pattern created in or on the sample.

In FIG. 13 the image of the illumination unit (2) is moved by means of a linear (97) and/or tilting (101) movement of the dichroic and/or semi-transparent mirror (115), which corresponds to the phase shift of the illumination pattern projected into or onto the sample. The tube lens (105) images the intermediate image (113), while the dichroic or semi-transparent mirror is located in a position of the beam path where the light is essentially collimated. The optical units (103) and (104) (tube optics) preferably have similar spectral properties and are preferably constructed identically. This symmetry leads to the situation that, independent of wavelength, planes (3) and (13) are imaged via the optics (103) and (104), respectively, into planes within the sample close enough together, such that with good approximation they can be considered as conjugate planes. Therefore, one can do without an active spectral correction with mechanical moving parts, which makes the arrangement faster and less complex. Thus, there is an arrangement for structured illumination disclosed here, which, despite the use of different wavelengths, works without moving mechanical parts. The section of the microscope arrangement (110) shown in FIG. 13 is upgraded with structured illumination and does also display the camera port (111) with the associated tube lens (117), which was originally intended to produce a real image of the sample in plane (113), where the (119) is part of the collimated beam path (infinity beam path) of the microscope.

Figure 14:
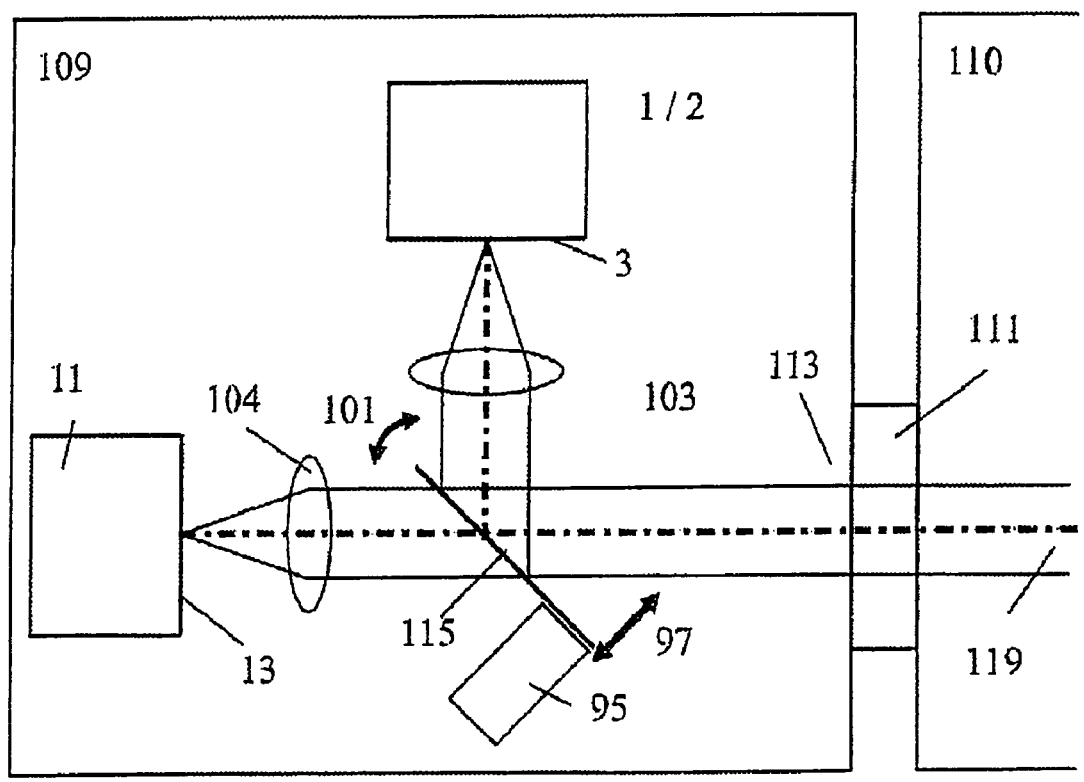
FIG. 14 is a block diagram showing an improvement to the upgrade unit, the upgrade unit having the tube optics and microscope removed.

Because the intermediate image in plane (113) is not strictly necessary for the arrangement proposed, the optical efficiency of the arrangement shown in FIG. 13 can be improved by a further modification shown in FIG. 14. Here the tube optics (117) of the microscope and (105) of the upgrade module (109) were removed, which leads to an extension of the infinity beam path of the microscope up to the dichroic or semi-transparent mirror (115) and beyond. In an advantageous implementation the tube optics (104) and (103) have the same properties as the original tube optics (117) of the microscope.

In a further embodiment, the integration of an arrangement for structured illumination into a microscope will be illustrated, where the labelling of the components is identical to FIG. 14 and the microscope features at least two camera ports (111).

Figure 15:
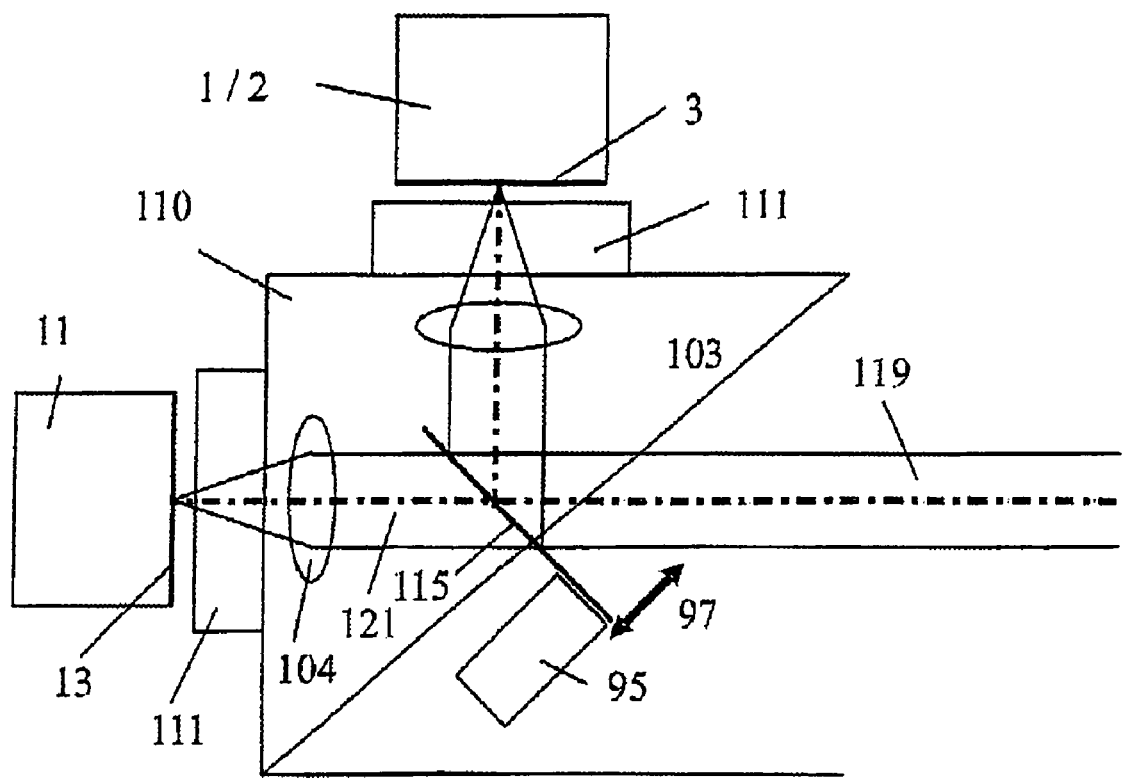
FIG. 15 is a block diagram showing a section of the microscope system formed in accordance with the present invention.

FIG. 15 shows a section of the microscope system (110), where (119) is part of the infinity beam path connected to the objective (5) of the microscope arrangement. In a practical arrangement, the beam paths may be folded once or several times by means of mirrors or beam splitters, which is not shown here for the sake of simplicity. On one of the camera ports (111), a detection unit (11) is mounted, where the real image formed by tube optics (104) is imaged onto the detection plane (13), which in turn is conjugated with plane (9) within the sample (10, not illustrated) into which illumination unit (1) respective (2) projects periodic illumination patterns. The detection unit (11) can feature several spatially resolving detectors. In the simplest case (11) is a camera mounted on the camera port (111) as usual. The illumination unit (1) or (2) is also mounted on a camera port (111). Here plane (3), which is conjugated with respect to planes (9) on or in the sample and plane (13) on the detection unit, is adjusted in exactly the location where usually a standard spatially resolving detector is mounted. The tube optics (103), that is usually employed to form a real image on a spatially resolving detector, is now used for imaging of the illumination unit and the mask or its image located in plane (3) into the sample. The original microscope arrangement (110) did provide a beam splitter instead of the dichroic beam splitter or semi-transparent mirror (115) which was supposed to distribute the detection light between the two camera ports (111). It is the function of the installed element (115) to split the illumination light from the illumination unit (1) or (2) from the detection light originating from the sample. In case the previously described illumination unit (1) is used, which features means for manipulating the phase of the illumination pattern projected onto or into the sample, a fixed, non-movable dichroic filter respective semi-transparent mirror (115) is used and the actuator (95) is omitted. If the less complex illumination unit (2) without the feature for phase control is used, element (115) can be moved with the help of actuator (95), which allows manipulation of the phase of the illumination pattern projected onto or into the sample by means of a lateral movement (97) and/or tilting. In arrangements suitable for fluorescence, element (115) can be for example in the form of a multi-band dichroic mirror. It should be pointed out that the use of an arrangement as shown in FIG. 15 requires removing or replacing the original beam-splitter of the microscope arrangement (110, not shown in the figure) with a mirror. Use of both the camera ports (111) has the advantage that both tube optics (103) and (104) (can) have identical spectral properties and a slow, mechanical chromatic correction according to the state of the art is not necessary. Should the microscope arrangement have more than two camera ports (111), the detection beam path (121) can be split into two or more paths after passing element (115) and can be guided towards the detection units (11) mounted on the appropriate camera ports.

In FIGS. 14 and 15, the tube optics (104) may be replaced with the unit from FIG. 9 for the simultaneous detection of different (e.g. spectral) channels on a single detector. Here the splitting into two channels is shown. The position of the detection unit shown in FIG. 9 is within the infinity beam path immediately behind the beam splitter, which separates the illumination light from the detection light. This placement even before the intermediate image has the advantage of a further increased optical efficiency, in contrast to the common arrangement after the real intermediate image, such as within unit (11).

The method according to the invention can be summarised as follows:

In a first step, one or more illumination patterns that are later also used for the generation of optical section images are projected onto a known calibration object. From this data or the image data for the calculation of the optical section image itself, the local phase of the projected pattern and as an option the local period of the structure and/or the intensity distribution of the projection steps is determined for every location on the detector. One can operate without the calibration measurement, if the local phase and period of the illumination pattern projected can be determined from image data that is recorded later in the process.

In further steps of the process, which may be repeated a number of times and for several wavelengths and different axial positions of the sample, there are two patterns projected onto the sample for each optical section image calculated with the help of the local phases and grating frequency of the illumination distribution on the detector. The implementations of structured illumination according to the state of the art require at least three projection steps for the creation of one optical section image and are therefore less efficient. In addition, arrangements according to the invention were proposed that perform the projection of the two illumination patterns without moving mechanical elements and in one embodiment even simultaneously. The selection of the light distributions projected can be accomplished via electronic control of light sources and/or optical switches. Further arrangements according to the invention allow the change of the imaging wavelength without moving of mechanical elements.

A calibration measurement for the determination of the local phases and grating frequencies has to be performed only in case of a change in the optical system, such as a change of the objective lens and perhaps when a new wavelength is used for the first time. The calibration measurement can be omitted when the determination is possible in sufficient quality from the image data recorded and when the required computing time can be tolerated.

The invention claimed is:

1. Arrangement for the generation of optical section images, consisting of an illumination unit, an optical arrangement for the imaging of the sample onto at least one spatially resolving detector, focussing means as well as a signal processing unit, for the implementation of a method for optical reproduction with depth discrimination, wherein the illumination unit, without any moving mechanical elements, creates each with only two different illumination distributions in respective on the sample, the illumination distributions have a periodicity in at least one spatial direction, the sample plane in which the illumination distribution is created is conjugated with respect to the plane of the corresponding spatially resolving detector, the light distributions within the sample resulting from the interaction with the illumination light are registered sequentially or simultaneously on said one or more spatially resolving detectors and fed to the signal processing unit in real-time for the calculation and generating of an optical section image wherein furthermore two illumination distributions are simultaneously projected and detected, where the light used for both projections is different with respect to polarization and/or spectral composition, where these different properties of the illumination light lead to different properties of the light distributions simultaneously emitted from the sample and these properties of the light emitted from the sample are used to separate the illumination patterns on the detection side.

2. Arrangement as defined in claim 1, wherein for the calibration of the light distribution registered on one or more detectors, especially the phase and/or the local period of the illumination pattern and/or the uniformity there is a calibration object, which is inserted instead of the sample or can be brought into position in the optical system or mounted in an image plane conjugated with the sample, where the calibration object preferably has homogeneous and/or known sample properties and is preferably flat.

3. Arrangement for the generation of optical section images as defined in claim 1,
wherein
the one or more spatially resolving detectors detect fluorescence and/or luminescence light emitted from the sample, where temporal modulation of the excitation by means of the illumination unit is implemented in combination with a synchronised or temporally resolved detection and the fluorescence and/or luminescence lifetime is determined.

4. Arrangement for the generation of optical section images as defined in claim 1,
wherein
the illumination unit for the generation of the illumination distributions in respective on the sample, uses a mask in transmission and/or reflection or a phase mask or a pixelated element or the illumination pattern is produced by the interference of plane waves.

5. Arrangement for the generation of optical section images as defined in claim 1,
wherein
the illumination unit generates two illumination distributions, which are displaced to each other by 180 degrees.

6. Arrangement for the generation of optical section images as defined in claim 1,
wherein
the two illumination distributions are generated within the illumination unit by means of front illumination or back illumination of a mask structure.

7. Arrangement for the generation of optical section images as defined in claim 1,
wherein
the arrangement allows a switching of the spectral composition of the light emitted by the illumination unit and/or the light registered by the at least one spatially resolving detectors.

8. Arrangement for the generation of optical section images, consisting of an illumination unit, an optical arrangement for the imaging of the sample onto at least one spatially resolving detector, focussing means as well as a signal processing unit, especially for the implementation of a method for the generation of optical section images by means of structured illumination of the sample, where illumination distributions with periodicity in at least one spatial direction are projected into a sample plane and light reflected on the sample and/or scattered and/or emitted fluorescence light and/or luminescence light is made to form an image on a spatially resolving detector,
wherein the method includes
a calibration step, in which the local phase and/or the local period of the illumination distribution are determined for every location on the detector, and
in the sample scanning mode,
for the calculation of each optical section image two illumination distributions are projected into respective onto the sample and the resulting light distributions are made to form an image on the detector,
the process steps of projection and detection of two illumination distributions can be repeated any desired number of times, especially for different focal positions of the sample and/or different illumination wavelengths, and
that from the intensity distributions with the help of the local phase and/or the local period at least one optical section image is calculated from the intensity distributions recorded,
wherein
the illumination unit creates two different illumination distributions in respective on the sample, the illumination distributions have a periodicity in at least one spatial direction, the sample plane in which the illumination distribution is created is conjugated with respect to the plane of the corresponding spatially resolving detector, the light distributions within the sample resulting from the interaction with the illumination light are registered sequentially or simultaneously on said one or more spatially resolving detectors and fed to the signal processing unit for the calculation of an optical section image,
and wherein
the two illumination distributions are configured within the illumination unit by means of electronic switching of light sources and/or the switching of optical fibre switches.

9. Arrangement for the generation of optical section images, consisting of an illumination unit for the generation of illumination distributions in respective on the sample, at least one spatially resolving detector for the registration of signals from the sample, focussing means as well as a signal processing unit, especially for the implementation of a method for the generation of optical section images by means of structured illumination of the sample, where illumination distributions with periodicity in at least one spatial direction are projected into a sample plane and light reflected on the sample and/or scattered and/or emitted fluorescence light and/or luminescence light is made to form an image on a spatially resolving detector,
wherein the method includes
a calibration step, in which the local phase and/or the local period of the illumination distribution are determined for every location on the detector, and
in the sample scanning mode,
for the calculation of each optical section image two illumination distributions are projected into respective onto the sample and the resulting light distributions are made to form an image on the detector,
the process steps of projection and detection of two illumination distributions can be repeated any desired number of times, especially for different focal positions of the sample and/or different illumination wavelengths, and
that from the intensity distributions with the help of the local phase and/or the local period at least one optical section image is calculated from the intensity distributions recorded,
and wherein
the phase shift of the structure projected by the illumination unit and optionally the chromatic correction, which means matching of the sample plane in which the illumination pattern is created with the plane imaged onto one or more detectors, is accomplished by means of linear motion or tilting of a mirror or dichroic mirror, which is involved in imaging the illumination unit into the sample.

10. Arrangement for the generation of optical section images, consisting of an illumination unit for the step-wise generation of several light distributions in respective on the sample, at least one spatially resolving detector for the registration of light distributions in respective on the sample, focussing means for the selection of the sample plane as well as a signal processing unit, especially for the implementation of a method for the generation of optical section images by means of structured illumination of the sample, where illumination distributions with periodicity in at least one spatial direction are projected into a sample plane and light reflected on the sample and/or scattered and/or emitted fluorescence light and/or luminescence light is made to form an image on a spatially resolving detector, wherein the method includes a calibration step, in which the local phase and/or the local period of the illumination distribution are determined for every location on the detector, and in the sample scanning mode, for the calculation of each optical section image two illumination distributions are projected into respective onto the sample and the resulting light distributions are made to form an image on the detector, the process steps of projection and detection of two illumination distributions can be repeated any desired number of times, especially for different focal positions of the sample and/or different illumination wavelengths, and that from the intensity distributions with the help of the local phase and/or the local period at least one optical section image is calculated from the intensity distributions recorded, and wherein the axial chromatic aberration is compensated by inserting one or more correction elements, preferably in the collimated section of the beam path after the output from the illumination unit, and/or in the pupil plane of the objective or a plane conjugated with it and/or in one or more spectral channels of the spatially resolving detection system, where the correction elements preferably contain diffractive optical elements or holograms and a change of the imaging wavelength does not require mechanical movement of the elements involved in the projection of the illumination structure and a potentially remaining chromatic axial aberration at the location of the sample is compensated by means of software during data acquisition or by means of an axial movement of the sample.

11. Arrangement for the generation of optical section images, consisting of an illumination unit for the generation of light distributions in respective on the sample, at least one spatially resolving detector for the registration of light distributions in respective on the sample, focussing means for the selection of the sample plane as well as a signal processing unit, especially for the implementation of a method for the generation of optical section images by means of structured illumination of the sample, where illumination distributions with periodicity in at least one spatial direction are projected into a sample plane and light reflected on the sample and/or scattered and/or emitted fluorescence light and/or luminescence light is made to form an image on a spatially resolving detector, wherein the method includes a calibration step, in which the local phase and/or the local period of the illumination distribution are determined for every location on the detector, and in the sample scanning mode, for the calculation of each optical section image two illumination distributions are projected into respective onto the sample and the resulting light distributions are made to form an image on the detector, the process steps of projection and detection of two illumination distributions can be repeated any desired number of times, especially for different focal positions of the sample and/or different illumination wavelengths, and that from the intensity distributions with the help of the local phase and/or the local period at least one optical section image is calculated from the intensity distributions recorded;

and wherein the beam paths for illumination and detection are optically identical with respect to their axial chromatic correction, where in particular they can be constructed identically, which make a mechanical re-adjustment of optical elements for the adjustment of the axial chromatic aberration during a change of wavelength obsolete.

12. Arrangement for the generation of optical section images in a microscope as defined in claim 11, wherein a spectral separation into one or more spectral channels for the simultaneous projection onto only one spatially resolving detector is done immediately after a dichroic beam splitter in the infinity beam path, where said beam splitter performs the separation of illumination light and detection light and the separation in spectral channels is performed before the formation of an intermediate image.

13. Arrangement for the generation of optical section images, consisting of an illumination unit for the generation of light distributions in respective on the sample, at least one spatially resolving detector for the registration of light distributions in respective on the sample, a microscope arrangement, focussing means for the selection of the sample plane as well as a signal processing unit, especially for the implementation of a method for the generation of optical section images by means of structured illumination of the sample, where illumination distributions with periodicity in at least one spatial direction are projected into a sample plane and light reflected on the sample and/or scattered and/or emitted fluorescence light and/or luminescence light is made to form an image on a spatially resolving detector, wherein the method includes a calibration step, in which the local phase and/or the local period of the illumination distribution are determined for every location on the detector, and in the sample scanning mode, for the calculation of each optical section image two illumination distributions are projected into respective onto the sample and the resulting light distributions are made to form an image on the detector, the process steps of projection and detection of two illumination distributions can be repeated any desired number of times, especially for different focal positions of the sample and/or different illumination wavelengths, and that from the intensity distributions with the help of the local phase and/or the local period at least one optical section image is calculated from the intensity distributions recorded;

and wherein a module comprising the illumination unit as well as the detection unit is connected to the camera port of the microscope arrangement, where the module contains a beam splitter for the separation of illumination light and detection light and the original beam splitter of the microscope was removed respective replaced by a mirror.

* * * * *